(12) United States Patent
McMahon

(10) Patent No.: US 11,033,196 B2
(45) Date of Patent: Jun. 15, 2021

(54) DIGITAL RANGE GATED RADIO FREQUENCY SENSOR

(71) Applicant: RESMED SENSOR TECHNOLOGIES LIMITED, Clonskeagh (IE)

(72) Inventor: Stephen McMahon, Dublin (IE)

(73) Assignee: ResMed Sensor Technologies Limited

(*) Notice: Subject to any disclaimer, the term of this patent is extended or adjusted under 35 U.S.C. 154(b) by 350 days.

(21) Appl. No.: 15/751,683

(22) PCT Filed: Aug. 16, 2016

(86) PCT No.: PCT/EP2016/069413
§ 371 (c)(1),
(2) Date: Feb. 9, 2018

(87) PCT Pub. No.: WO2017/029284
PCT Pub. Date: Feb. 23, 2017

(65) Prior Publication Data
US 2018/0239014 A1 Aug. 23, 2018

Related U.S. Application Data

(60) Provisional application No. 62/205,129, filed on Aug. 14, 2015.

(51) Int. Cl.
*G01S 13/89* (2006.01)
*A61B 5/0507* (2021.01)
(Continued)

(52) U.S. Cl.
CPC .............. *A61B 5/0507* (2013.01); *A61B 5/11* (2013.01); *A61B 5/4809* (2013.01);
(Continued)

(58) Field of Classification Search
CPC .............................. G01S 13/89; A61B 5/0507
See application file for complete search history.

(56) References Cited

U.S. PATENT DOCUMENTS

| 4,197,537 A | 4/1980 | Follen et al. |
| 5,361,070 A | 11/1994 | McEwan |

(Continued)

FOREIGN PATENT DOCUMENTS

| EP | 1057046 A2 | 12/2000 |
| EP | 2051098 A1 | 4/2009 |

(Continued)

OTHER PUBLICATIONS

International Preliminary Report on Patentability dated Oct. 30, 2017.

(Continued)

*Primary Examiner* — Marcus E Windrich
(74) *Attorney, Agent, or Firm* — Botos Churchill IP Law LLP

(57) ABSTRACT

A digitally implemented radio frequency sensor for physiology sensing may be configured to generate oscillation signals for emitting radio frequency pulses for range gated sensing. The sensor may include a radio frequency transmitter configured to emit the pulses and a receiver configured to receive reflected ones of the emitted radio frequency pulses under control of a microcontroller. The received pulses may be processed by the microcontroller to detect physiology characteristics such as motion, sleep, respiration and/or heartbeat. The microcontroller may be configured to generate timing pulses such as with a pulse generator for transmission of radio frequency sensing pulses. The microprocessor may sample received signals, such as in phase and quadrature phase analogue signals, to implement digital demodulation and baseband filtering of the received signals.

56 Claims, 14 Drawing Sheets

(51) Int. Cl.
*A61B 5/11* (2006.01)
*A61B 5/00* (2006.01)
*G01S 13/18* (2006.01)
*G01S 13/56* (2006.01)
*G01S 7/288* (2006.01)
*G01S 7/282* (2006.01)
*H03B 5/18* (2006.01)
*G01S 13/02* (2006.01)
*A61B 5/08* (2006.01)
*A61B 5/024* (2006.01)

(52) U.S. Cl.
CPC ............ *A61B 5/7225* (2013.01); *G01S 7/282* (2013.01); *G01S 7/288* (2013.01); *G01S 13/0209* (2013.01); *G01S 13/18* (2013.01); *G01S 13/56* (2013.01); *H03B 5/187* (2013.01); *A61B 5/024* (2013.01); *A61B 5/0816* (2013.01); *A61B 5/1102* (2013.01)

(56) References Cited

U.S. PATENT DOCUMENTS

| | | | |
|---|---|---|---|
| 5,682,164 A | 10/1997 | McEwan | |
| 5,966,090 A | 10/1999 | McEwan | |
| 6,426,716 B1* | 7/2002 | McEwan | G01S 13/04 329/311 |
| 7,002,511 B1* | 2/2006 | Ammar | G01S 7/032 342/118 |
| 7,952,515 B2* | 5/2011 | McEwan | G01S 13/225 342/156 |
| 10,376,670 B2* | 8/2019 | Shouldice | G10L 15/26 |
| 2007/0018890 A1* | 1/2007 | Kulyukin | G01C 21/005 342/357.31 |
| 2009/0203972 A1* | 8/2009 | Heneghan | A61B 5/0816 600/301 |
| 2010/0214158 A1* | 8/2010 | McEwan | G01S 13/18 342/173 |
| 2014/0024917 A1* | 1/2014 | McMahon | A61B 5/7225 600/407 |
| 2014/0276245 A1 | 9/2014 | Tsutsumi et al. | |
| 2015/0216424 A1 | 8/2015 | Stephen et al. | |
| 2015/0331081 A1* | 11/2015 | Wharton | G01C 21/3632 342/443 |

FOREIGN PATENT DOCUMENTS

| | | |
|---|---|---|
| JP | 2003524751 A | 8/2003 |
| JP | 2013094340 A | 5/2013 |
| WO | 9942856 A2 | 8/1999 |
| WO | 2009083017 A1 | 7/2009 |
| WO | 2014015238 A1 | 1/2014 |

OTHER PUBLICATIONS

JP Office Action dated Sep. 1, 2020 for JP Patent Application No. 2018507531.

* cited by examiner

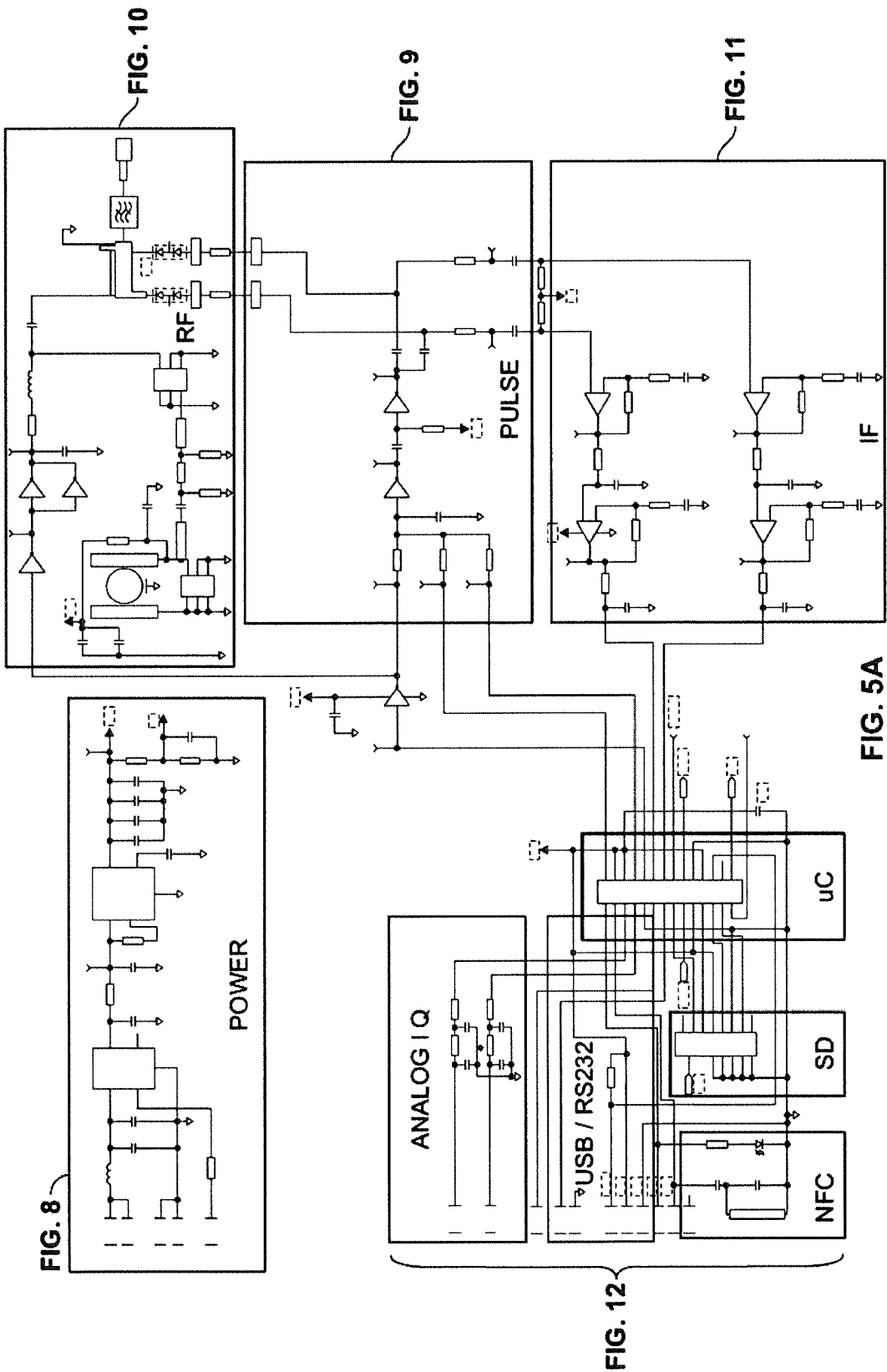

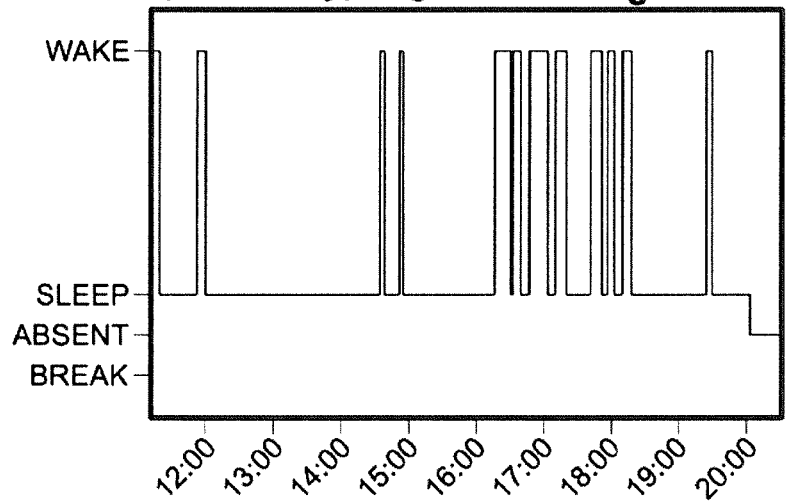
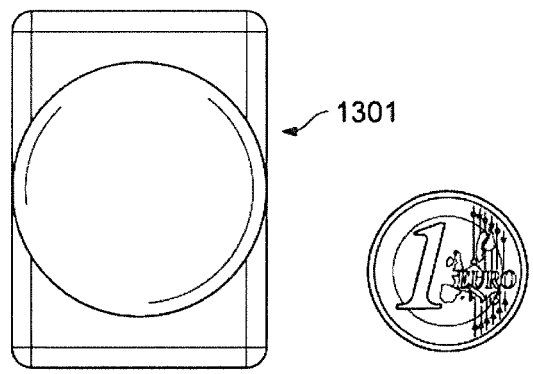
FIG. 13

DIGITAL RANGE GATED RADIO FREQUENCY SENSOR

CROSS REFERENCE TO RELATED APPLICATIONS

The present application is a national phase entry under 35 U.S.C. § 371 of International Application No. PCT/EP2016/069413 filed Aug. 16, 2016, published in English, which claims priority from U.S. Provisional Patent Application No. 62/205,129 filed Aug. 14, 2015, all of which are incorporated herein by reference.

FIELD OF THE TECHNOLOGY

The present technology relates to radio frequency sensors for detection of characteristics of moving objects and living subjects. More particularly, it relates to circuits of such sensors, such as range gated radio frequency motion sensors implemented digitally with microcontrollers, with particular emphasis on detecting physiological characteristics of a user.

BACKGROUND OF THE TECHNOLOGY

Continuous wave (CW) Doppler radar motion sensors emit a continuous wave radio frequency (RF) carrier signal and mix the transmitted RF signal with the return echoes to produce a difference frequency equal to the Doppler shift produced by a moving target. These sensors do not have a definite range limit (i.e., they can receive signals for both near and far objects, with the received signal being a function of radar cross section). This can lead to false triggers, i.e., motion artefact interference. They may also have an undesirably high sensitivity at close range that leads to false triggering.

A pulse Doppler motion sensor is described in U.S. Pat. No. 4,197,537 to Follen et al. A short pulse is transmitted and its echo is self-mixed with the transmitted pulse. The pulse width defines the range-gated region. When the transmit pulse ends, mixing ends and target reflections arriving after the end of the transmit pulse are not mixed and are thereby gated out.

A Differential pulse motion sensor disclosed in U.S. Pat. No. 5,966,090, "Differential Pulse Radar Motion Sensor," to McEwan, alternately transmits two pulse widths. It then subtracts the responses from each width to produce a range gated sensing region having a fairly constant response versus range.

Impulse radar, such as that described in U.S. Pat. No. 5,361,070, "Ultra-Wideband Radar Motion Sensor," to McEwan produces a very narrow sensing region that is related to the transmitted impulse width. A two-pulse radar motion sensor, as described in U.S. Pat. No. 5,682,164, "Pulse Homodyne Field Disturbance Sensor," to McEwan, transmits a first pulse and after a delay generates a second pulse that mixes with echoes from the first pulse. Thus a range gated sensing band is formed with defined minimum and maximum ranges. UWB radar motion sensors have the disadvantage of not having global RF regulatory acceptance as an intentional radiator. They also can have difficulty sensing objects at medium ranges and in some embodiments can be prone to RF interference.

A modulated pulse sensor is described in U.S. Pat. No. 6,426,716 to McEwan. The range gated microwave motion sensor includes adjustable minimum and maximum detection ranges. The apparatus includes an RF oscillator with associated pulse generating and delay elements to produce the transmit and mixer pulses, a single transmit (TX)/receive (RX) antenna or a pair of separate TX and RX antennas, and an RF receiver, including a detector/mixer with associated filtering, amplifying and demodulating elements to produce a range gated signal from the mixer and echo pulses.

In U.S. Pat. No. 7,952,515, McEwan discloses a particular holographic radar. It adds a range gate to holographic radar to limit response to a specific downrange region. McEwan states that cleaner, more clutter-free radar holograms of an imaged surface can be obtained, particularly when penetrating materials to image interior image planes, or slices. The range-gating enables stacked hologram technology, where multiple imaged surfaces can be stacked in the downrange direction.

In U.S. Patent Application Publ. no. 2010/0214158, McEwan discloses an RF magnitude sampler for holographic radar. McEwan describes that the RF magnitude sampler can finely resolve interferometric patterns produced by narrowband holographic pulse radar.

In U.S. Patent Application Publ. no. US-2014-0024917-A1, McMahon, et al. teach an analog range gated radio frequency physiology sensor.

There may be a need to improve sensors for pulse radio frequency sensing such as in the case of physiological characteristic detection.

SUMMARY OF THE TECHNOLOGY

One aspect of some embodiments of the present technology relates to an improved circuit design with digital components for a sensor for detecting physiology characteristics with radio frequency signals.

Another aspect of some embodiments of the technology relates to such a sensor with a circuit configured to generate pulsed radio frequency (RF) signals such as for range gating.

A still further aspect of some embodiments of the technology relates to a sensor with a circuit with improved oscillator design.

An additional aspect of some embodiments of the technology relates to such a sensor configured for improved RF oscillator frequency stability that also maintains fast switching characteristics desirable for range gating.

A further object of some embodiments of the technology is to provide an RF sensor that is amenable to radio frequency regulatory requirements as an intentional radiator.

Some embodiments of the present technology may include a radio frequency motion sensor. The sensor may include a radio frequency transmitter. The transmitter may be configured to emit radio frequency pulses. The sensor may also include a receiver configured to receive reflected ones of the emitted radio frequency pulses. The radio frequency transmitter may include a microcontroller. The microcontroller may be configured to generate timing pulses. The radio frequency transmitter may also include a pulse generator configured to generate signal pulses in response to receiving the timing pulses; an oscillator, such as a dielectric resonator, configured to generate a stable radio frequency oscillating signal; and a switched circuit coupled to the pulse generator and the oscillator. The switch circuit may be configured to generate a pulsed radio frequency oscillating signal having a dominant frequency derived from the oscillator.

Some versions of the present technology may include a digital radio frequency motion sensor. The sensor may include a radio frequency transmitter configured to emit radio frequency pulses. The sensor may include a receiver configured to receive reflected ones of the emitted radio frequency pulses. The radio frequency transmitter may include a microcontroller configured to generate timing pulses; a pulse generator configured to generate signal pulses in response to the timing pulses; an oscillator configured to generate a stable radio frequency oscillating signal; and a switched circuit coupled to the pulse generator and the oscillator. The switch circuit may be configured to generate a pulsed radio frequency oscillating signal whose frequency is derived from the oscillator. The oscillator comprises a dielectric resonator.

In some cases, the pulse generator may include a logic gate circuit configured to receive a timing signal generated by the microcontroller. The microcontroller may be coupled with the receiver to sample a signal from the receiver representing phase and/or magnitude differences between the received reflected ones of the emitted radio frequency pulses and the emitted radio frequency pulses. The receiver may include a mixer. The mixer may include a switched magnitude detector. The microcontroller may control timing of the mixer's operation. The microcontroller may be configured to digitally control the timing of the mixer. The microcontroller may be configured to digitally demodulate the signal from the receiver. In some cases, the receiver may generate in phase and quadrature phase signals for sampling at inputs to the microcontroller. In some versions of the sensor, the microcontroller may be configured to generate an indicator of any one or more of respiration, sleep and heart rate information from one or more digitally demodulated signals from the receiver In some cases, the microcontroller may be configured to trigger sensor operation by turning the sensor on and off. The microcontroller may be configured to control storing of data from received signals in epochs. The sensor may also include a memory, wherein the memory stores the epochs. The memory may be or include one or more of SD cards, microSD cards, and flash. The memory may be integrated into the microcontroller. The sensor is configured for wireless transmission from the sensor of data derived from received signals. The wireless transmission may include NFC communications.

The microcontroller may be configured to digitally filter one or more signals from the receiver. The microcontroller may be configured to digitally filter one or more baseband signals from the receiver. The microcontroller may be configured to digitally amplify one or more baseband signals from the receiver. In some cases, sensor may also include a digital or analogue output connection. The digital or analogue output connection may be a RS232, serial or USB connection. The sensor may include an analog output, and the microcontroller may be configured to convert digital signals received from the receiver into analogue signals for output via the analog output. The analog signals comprise a pulse width modulated signal.

The sensor may also include a housing, wherein the sensor is contained within the housing. The transmitter and receiver may have a single printed circuit board and the microcontroller may be a chip coupled, e.g., soldered, to the printed circuit board.

The receiver may comprise two detectors for mixing the emitted radio frequency (RF) pulses and the received reflected ones of the emitted radio frequency pulses. The two detectors may include one magnitude detector for in-phase signals and one magnitude detector for quadrature phase signals. Each magnitude detector may be configured to switch on, at a first defined point in time t1 and for a first defined time duration T1 within each one of a first number of RF pulses, to effect range gating capability of the sensor. In some cases each detector may switched at a second defined point in time t0 for a second defined time duration T0 within each one of a second number of RF pulses, the first defined point in time t1 being different from the second defined point in time t0. In some versions, the first number of RF pulses may be equal to the second number of RF pulses and/or the first or the second number of RF pulses may be a number of consecutive pulses.

The detectors may each modulate the mixed pulses at an intermediate frequency that is higher than a baseband frequency. Each detector may alternate between being switched on at the first defined time t1, during the first number of RF pulses, and being switched on at the second defined time t0, during the second number of further RF pulses. In some instances the first time duration T1 is equal to second time duration T0. The first defined time t1 can be different from the second defined time t0.

In some cases the receiver may further include a preamplifier or an amplifier for amplifying the modulated mixed pulses at the intermediate frequency.

The microcontroller may be configured to demodulate the amplified modulated mixed pulses into baseband signals. The microcontroller may digitally control the receiver and radio frequency transmitter to automate the change of at least some of their parameters.

Some versions of the present technology may include a circuit for generating signals to produce radio frequency pulses for range gated physiology sensing. The circuit may include a microcontroller, which may be configured to generate timing pulses. The circuit may include a pulse generator configured to generate signal pulses in response to receiving timing pulses, such as form the microcontroller. The circuit may include an oscillator configured to generate a radio frequency oscillating signal. The circuit may include a switched circuit coupled to the pulse generator and the oscillator. The switched circuit may be configured to generate a pulsed radio frequency oscillating signal in accordance with the signal pulses and radio frequency oscillating signal. The circuit may include an antenna feed coupled with an output of the switched circuit to accept the pulsed radio frequency oscillating signal and emit radio frequency pulses in accordance with the pulsed radio frequency oscillating signal via an antenna. The antenna feed may be configured to receive reflected ones of the emitted radio frequency pulses.

In some cases, the circuit may include a set of magnitude detectors coupled with the antenna feed. The magnitude detectors may detect signals received with the antenna feed based on signals generated from the switched circuit. The microcontroller may be configured to sample one or more outputs of the magnitude detectors. The outputs of the magnitude detectors may include an in phase signal and a quadrature phase signal representing phase and/or magnitude differences between the received reflected ones of the emitted radio frequency pulses and the emitted radio frequency pulses. The microcontroller may be configured to digitally demodulate outputs of the magnitude detectors. The microcontroller may be configured to digitally filter outputs of the magnitude detectors. The microcontroller may be configured to digitally filter one or more baseband signals derived from the magnitude detectors. The microcontroller may be configured to digitally amplify one or more baseband signals from the magnitude detectors. The oscillator may include a dielectric resonator. The pulse generator may include a logic gate circuit configured to receive a timing signal generated by the microcontroller.

The microcontroller may be configured to generate an indicator of any one or more of respiration, sleep and heart rate information based on one or more signals received via the antenna feed. Thee microcontroller may be configured to trigger the circuit's sensing operations by selectively turning transmissions on and off. The microcontroller may be configured to control storing of data from received signals in epochs. The circuit may also a memory interface. The memory interface may be one or more of SD card interface, a microSD card interface, and a flash memory interface. The circuit may also include a wireless transceiver for transmission of data derived from sensing signals. The wireless transmission may involve NFC communications.

The circuit may include a digital and/or analogue output connection. The digital or analogue output connection may include a RS232, serial and/or USB connection. The circuit may include an analog output (e.g., an output interface or connector), and the microcontroller may be configured to convert digital signals sensed by the circuit into analogue signals for output via the analog output. The analog signals may include a pulse width modulated signal. The circuit may include a single printed circuit board and the microcontroller may be a chip affixed (e.g., soldered) to the printed circuit board.

Other aspects, features, and advantages of this technology will be apparent from the following detailed description when taken in conjunction with the accompanying drawings, which are a part of this disclosure and which illustrate, by way of example, principles of the technology. Yet further aspects of the technology will be apparent from the appended claims.

BRIEF DESCRIPTION OF THE DRAWINGS

Further example embodiments of the technology will now be described with reference to the accompanying drawings, in which:

FIG. 5A is an schematic of a circuit, such as for a single printed circuit board (PCB), with an architecture of an example sensor circuit in some embodiments of the technology;

FIG. 13 is an illustration of an interface for displaying physiology data suitable for some embodiments of the disclosure.

DETAILED DESCRIPTION

1. Overview

Figure 1:
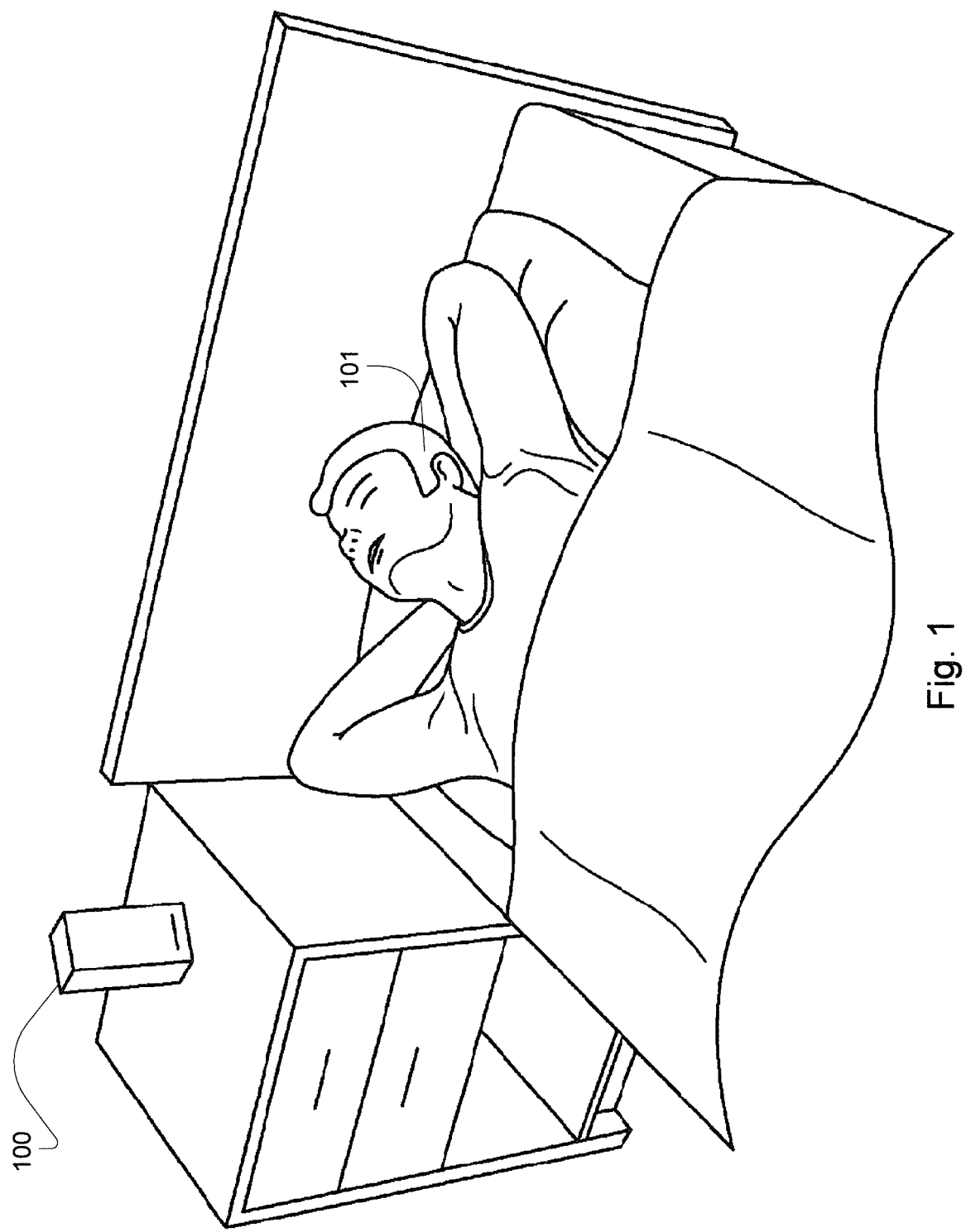
FIG. 1 is an illustration of an example detection apparatus suitable for implementation with a radio frequency physiology sensor of the present technology.

As illustrated in FIG. 1, some embodiments of the present technology may implement a radio frequency (RF) sensing or detection apparatus 100 having digital circuit components, such as one with a microcontroller or microprocessor involved in the RF sensing signal generation and/or signal (e.g., baseband, passband, etc.,) processing. The apparatus is useful for detecting physiological characteristics of a user 101 or patient in the vicinity of the apparatus. The sensor may be a standalone sensor or may be coupled with other apparatus, such as a respiratory treatment apparatus, so as to provide an automated treatment response based on an analysis of the physiological characteristics detected by the sensor of the apparatus. For example, a respiratory treatment apparatus with a controller and a flow generator may be configured with such a digital sensor and may be configured to adjust a pressure treatment generated at a patient interface (e.g., mask) in response to physiological characteristics detected by the digital sensor.

Other data can be gathered from the user by other sensing modules via a radio link, or directly from the medication dispenser, e.g., via an identification chip such as RFID (radio frequency ID), or from a measuring device such as a spirometer (peak flow meter). Additionally, further data can be gathered from the user via accelerometers, ECGs, Oximeters, etc. Additional data may also be gathered from the user by way of a keyboard, a touch sensitive pad, mouse, voice recording, etc.

With the inclusion of a microcontroller or microprocessor as part of the sensor circuit to control or participate in sensing operations of the sensor, increased functionality may be provided and a reduction in the complexity of circuitry may be realized The reduction in the amount circuitry may allow the size of the sensor may be reduced, thereby making the sensor small and portable. Additionally, the power consumption of the sensor may be reduced with respect to such a sensor essentially formed with analogue components, allowing the digital sensor to be powered by many different types of sources (e.g., mains power, battery power, etc.). As such, the cost, size, power consumption, and reliability of the sensor including a microcontroller may be improved over sensors containing complex analog circuitry.

The microcontroller may include control of the modulation and demodulation timing of other components within the sensor. As described in greater detail herein, the microcontroller may provide timing pulses to control the modulation and demodulation of transmitted and received RF signals to generate a baseband signal. The timing pulses may also control the timing of the transmission of RF signals by a transmitter as well as the receiving of the RF signals by a receiver. As such, the microcontroller may provide variable and dynamic range gating for detecting physiological characteristics of a user 101 or patient within a particular vicinity of the apparatus (i.e., the ability to manually or automatically adjust the range of the sensor to, for instance, monitor a room, monitor a sleeper at a different and/or changing sensing range (say 1 m distance for a subject close to the sensor, or 2.5 m for a subject further away from the sensor) etc.) Additionally, the timing pulses may lower the system noise floor and mitigate interference by dithering the timing of the transmitted RF signals. For example, in generating timing signals, the microcontroller may vary the timing of the timing signals to dither the timing of the transmitted RF pulses. Dithering of the timing when combined with averaging, that naturally occurs in the baseband filters, mitigates harmonic tones and interference.

Modulation of the baseband signal to an intermediate frequency (IF) signal, as well as the demodulation of the IF signal back to a baseband signal may be enhanced by the addition of a microcontroller to the sensor. The control of the generation and demodulation of the IF signal by the microcontroller may allow for complex digital synchronous demodulation schemes without the need for complex hardware to be added to the sensor. Further, the microcontroller may allow the sensor to utilize improved digital filter and noise reduction when compared to sensors with analog circuits.

A digitally implemented sensor of such an apparatus may employ a transmitter to emit radio frequency wave signals, such as radio frequency pulses for range gated sensing. A receiver, which may optionally be included in a combined device with the transmitter, may be configured to receive and process some, or all of, the transmitted radio frequency pulses that are reflected off of a user's body (e.g., head, torso, leg, arm, etc.) located in the vicinity of the sensor. Signal processing may be employed, such as with a microcontroller of the sensor that activates the sensor, to derive physiological characteristics based on the received reflected signals.

Figure 2:
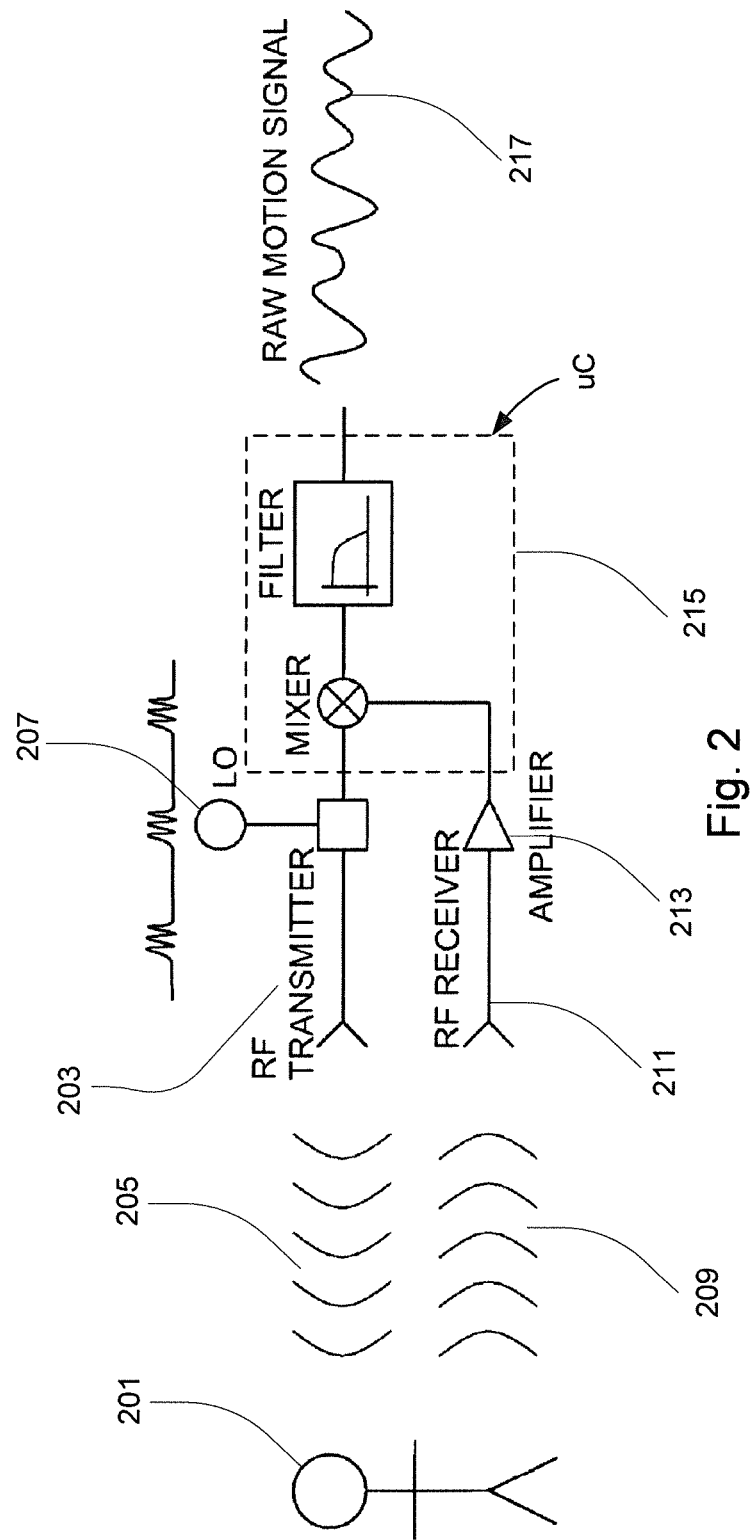
FIG. 2 is a diagram illustrating a conceptual structure and process flow for evaluation of sensor signals suitable for some embodiments of the technology.

For example, as illustrated in FIG. 2, the RF transmitter 203 transmits a radio-frequency signal 205 towards a subject, e.g., a human 201. The source of the RF signal may be a local oscillator (LO) 207, though other sources may be used. The reflected signal 209 is then received by an RF receiver 211 and amplified by an amplifier 213. The amplified reflected signal may then be mixed with a portion of the original signal by a microcontroller 215. The output of this mixed signal may then be filtered digitally by the microcontroller. The resulting signal may contain information about the movement, respiration and cardiac activity of the person, and is referred to as the raw motion sensor signal 217 and may be output as digital and/or analogue signal(s).

Figure 3:
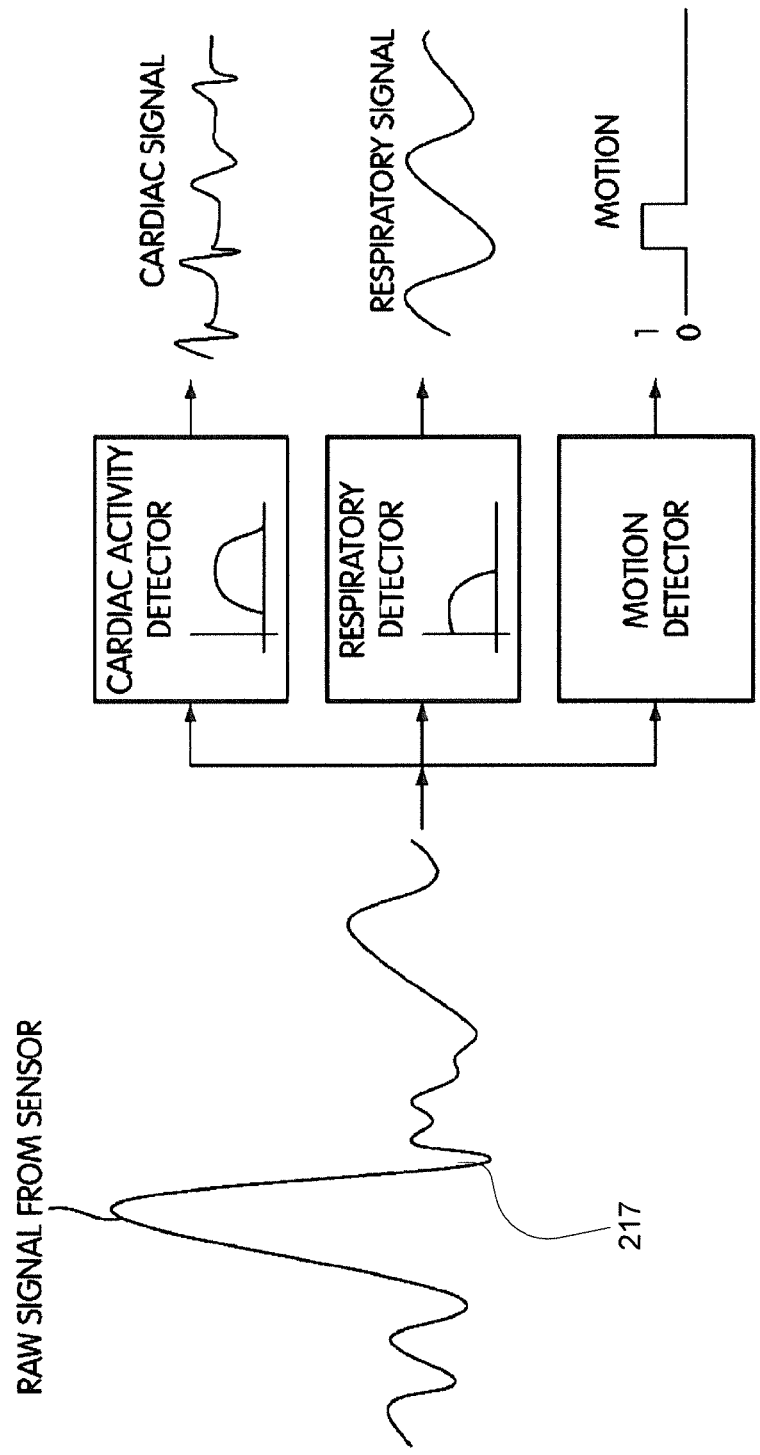
FIG. 3 is a depiction of further processing of sensor signals for the detection of example physiology indicators.

FIG. 3 is a diagram illustrating processing of the raw motion sensor signal to produce indicators of the physiological characteristics. The raw motion sensor signal 217 may generally contain components reflecting a combination of bodily movement, respiration, and cardiac activity. Bodily movement can be associated with the movement of a user's body and may be identified by a motion detector 330 which may implement movement detection algorithms, such as zero-crossing or energy envelope detection algorithms or other more complex algorithms. Bodily movements identified by the movement detection algorithms may be used to form a "motion on" or "motion off" indicator. For example, such movement detection algorithms may be implemented in accordance with the methodologies disclosed in U.S. Patent Application Publ. No. 2009/0203972, the entire disclosure of which is incorporated herein by reference. Further, a microcontroller, such as microcontroller 215, may execute the movement detection algorithms. The respiratory activity is typically in the range 0.1 to 0.8 Hz, and can be derived by filtering the original signal with a bandpass filter 320 with a passband in the 0.1 to 0.8 Hz region. The cardiac activity is reflected in signals at higher frequencies, and this activity can be accessed by filtering with a bandpass filter 310 with a passband of a range from 1 to 10 Hz. Such bandpass filtering may be accomplished by the microcontroller via algorithms running within the microcontroller.

2. Digital Sensor

A digital respiration and movement sensor may be a range gated RF motion detector. The digital sensor may be configured to accept a DC power supply input and provide digital and analogue motion channel outputs with both in phase and quadrature components of the respiration and movement signals of a person within the detection range. In the case of a pulsed RF motion sensor implemented with digital control, range gating can help to limit movement detection to only a preferred zone or range. Thus, detections made with the sensor may be within a defined distance from the sensor.

To achieve range gating in a digital pulsed RF motion detector system, including a microcontroller, the RF pulses should have a fast turn on and settling time characteristic. Although wideband RF oscillators with a low Q factor tuned circuit may be suitable for such embodiments, such wideband oscillators are prone to frequency stability issues. However, switching the wideband RF oscillator ON and OFF can allow the oscillator to generate RF pulses. Accordingly, embodiments of the present technology may improve RF oscillator frequency stability while maintaining the fast switching characteristics required for range gating.

Figure 4:
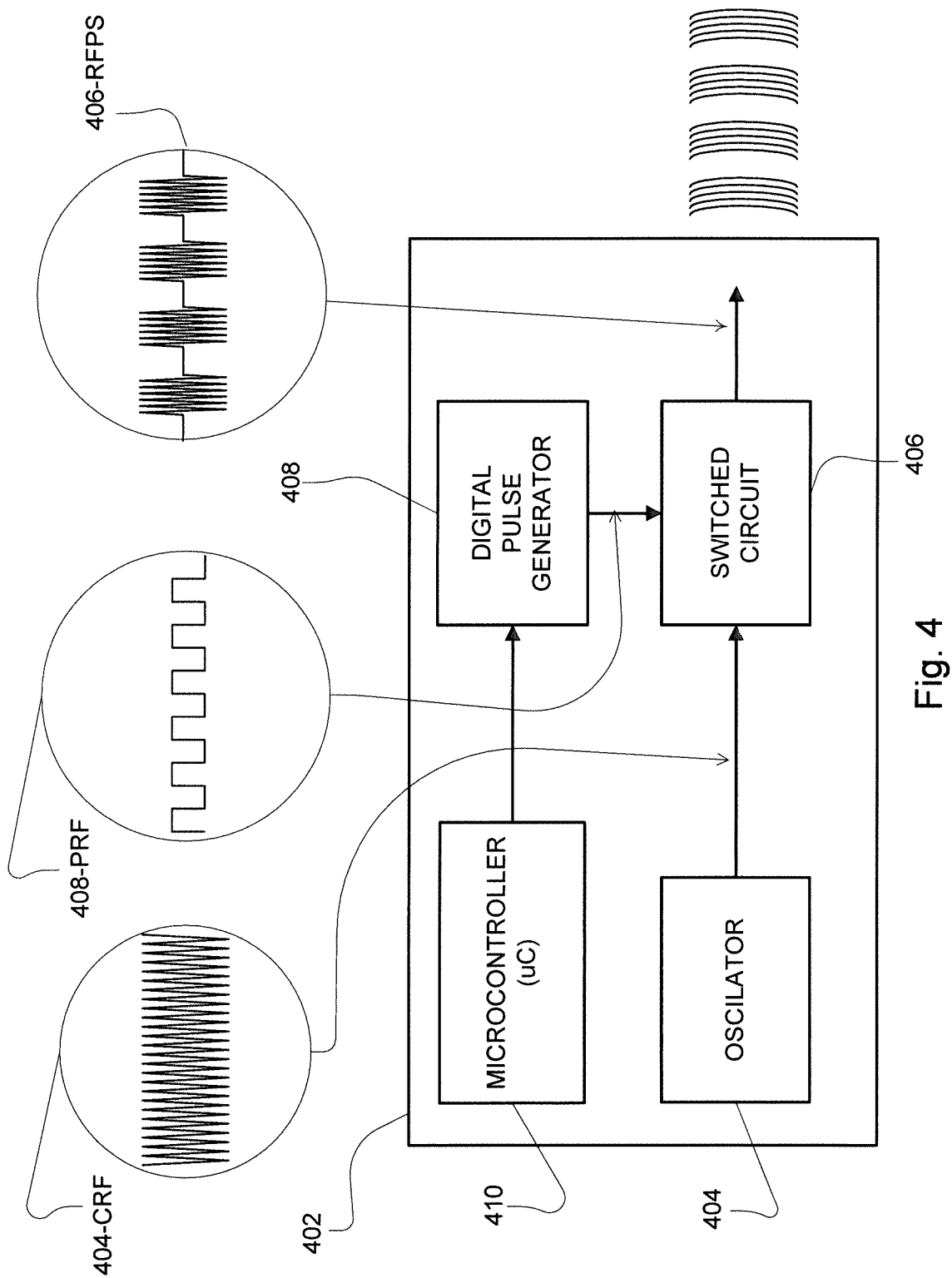
FIG. 4 shows example components involved in a generation of range gated radio frequency signals with switched oscillation in some embodiments of a sensor circuit for the present technology.

Illustrated in FIG. 4, is an example of a digital sensor 402 of the present technology which may employ an oscillator 404, such as a dielectric resonant oscillator (DRO). The DRO may be a high Q DRO, that is a narrowband oscillator (e.g., a DRO operating at 10.525 GHz). Such an oscillator may incorporate a puck of dielectric material. The DRO typically generates a stable RF frequency characteristic and is relatively immune to variation in temperature, humidity and component parasitics. However, it may have a very slow turn on time. The slow turn on time may result in the oscillator being unable to switch ON and OFF quickly enough to provide an RF signal suitable for a range gated system. For example, a typical DRO may switch ON about 1000 times too slowly to meet some sensor range gating requirements.

Accordingly, to address such issues, the oscillator 404 may be coupled with a switched oscillation circuit, such as a switched wideband oscillator 406 or a switched amplifier. In such a case, the DRO oscillator 404 may produce a stable RF oscillation signal 404-CRF (continuous radio frequency) when it is kept continuously ON during pulsed transmissions rather than being powered ON and OFF by switching the DRO oscillator's power source. The stable RF oscillation signal 404-CRF continuously output from the DRO oscillator 404 may then be applied to an input of the switched wideband oscillation circuit 406. Based on a timing pulse signal 408-PRF (pulse repetition frequency) output from a pulse generator 408 to an input of the switched wideband oscillation circuit 406, the switched wideband oscillation circuit 406 may generate the radio frequency pulse signals 406-RFPS used for range gating in synchrony with the pulse signal. The transmission of the pulsed RF signals may be from a suitable antenna and antenna feed (not shown in FIG. 4).

The timing of the pulse generator may be controlled by a timing signal from a microcontroller (uC) 410. In this regard, the timing signal from the microcontroller 410 may trigger the pulse generator 408, or in some cases the microcontroller 410 can serve as the pulse generator. For example, in response to the triggering pulses from the microcontroller, the pulse generator may generate a 1 MHz PRF 408-PRF, as well as a 8 kHz intermediate frequency (IF) demodulation pulse signals, described in detail herein (not shown in FIG. 4). The digital pulse generator circuit 408 generates the IF modulation pulse signals necessary to realize range gating under the control of the IF signal. By varying the time of these IF demodulation pulse signals, programmable range gating can be realized; this variation can be under the control of the microcontroller which in turn realizes such programmable range gating.

In the case of this implementation of the switched wideband oscillator, injection locking may be employed to stabilize the switched wideband oscillator to provide both frequency stability and fast oscillator turn on with good OFF attenuation characteristics. Thus, the switched wideband oscillation circuit 406 may be injection locked by the DRO oscillator 404. In the case of the implementation of the switched amplifier, the wideband amplification of the DRO oscillator's RF output signal can provide both frequency stability and an even faster turn on time.

Alternatively, in some embodiments, rather than implementing a switched oscillation circuit to generate the pulsed radio frequency signal as illustrated in FIG. 4, one or more semiconductor switches, such as in series, may be implemented to selectively shunt or pass the radio frequency signal. In such alternative embodiments, the switch or switches merely permit selective output of the radio frequency signal due to toggling of the switches. In this sense, the switch, as opposed to the switched oscillation circuit, merely passes the received oscillation signal at certain times. However, there are several disadvantages with such implementations. One such disadvantage of the semiconductor switch architecture is that the components are expensive at microwave frequencies. Another disadvantage with such a switching architecture is that RF signal attenuation (i.e., the ratio of ON signal level to OFF signal level) is low. A high attenuation is required to permit correct range gating performance. Multiple switches, such as in a "T" switch network, can be implemented to mitigate such attenuation issues but may undesirably increase its cost.

Figure 5:
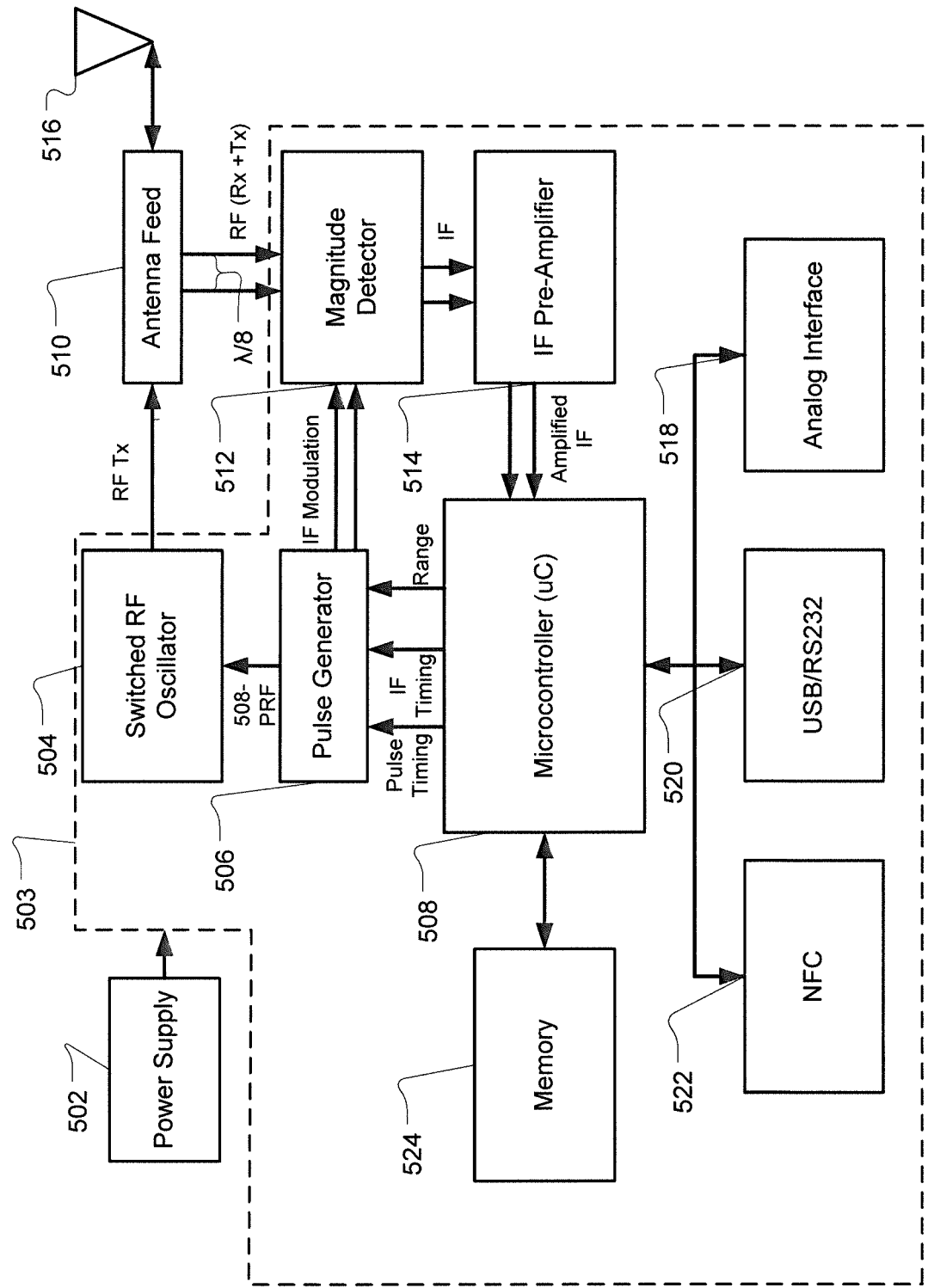
FIG. 5 is a schematic of components for an architecture of an example sensor circuit in some embodiments of the technology.

Example digital sensor circuit architectures according to some embodiments of the present technology are illustrated in the FIGS. 5 and 5A. The circuit may be a digital bio-motion sensor implemented as a pulse radar system operating in, for example, the microwave X-band at a frequency of 10.525 GHz. A high frequency may allow for RF pulse waveforms which have very sharp lead and end edges, resulting in a cleaner pulse signal. However, other suitable RF frequencies may be implemented. Some embodiments may optionally employ a method for modulation and demodulation of the pulse radar signal as described in U.S. Pat. No. 6,426,716, the entire disclosure of which is incorporated herein by reference.

As illustrated in FIGS. 5 and 5A, the digital sensor circuit may be formed by four main sections:

(1) a homodyning transceiver frontend section: This section may include the switched oscillation circuit 504, such as a switched 10.525 GHz wideband oscillator or switched amplifier, which may include a DRO oscillator, an antenna feed 510, antenna(s) 516, and a magnitude detector 512 for generation and reception of the pulsed RF radar signals;

(2) a pulse generator section: This section may include a pulse generator circuit 506. The generator may be configured to generate the pulse signals 508-PRF, 508-IF (IF standing for intermediate frequency) for modulation and demodulation of the RF radar signals (i.e., RF Tx, as shown in FIG. 5). The pulse generator may also be configured to generate IF modulation pulse signals for the modulation of the IF signals, as further shown in FIG. 5;

(3) a dual channel IF pre-amplifier 514 for the amplification of the received IF signals, which may subsequently be sent to the microcontroller 508, to produce an amplified baseband signal; and (4) a microcontroller 508 for generating the timing pulse signals which trigger the pulse generator 506. Additionally, the microcontroller may be programmed for digital filtering of the baseband signals (e.g., digital signal processing of the received raw motion signal to derive cardiac, respiratory and/or motion signals). The use of the microcontroller may eliminate the need for separate analog circuitry, resulting in reduced size, cost, and energy consumption by the sensor.

In addition to the above four sections, the digital sensor may also include sections for power management 502, memory storage devices 524 (i.e., SD), various input/output connections (i.e., Analog IQ 518, USB/RS232 520, NFC 522), and ECG electrodes (not shown.) As shown in FIG. 5A, all of the sections may be interconnected and controlled with the microcontroller.

The digitally implemented sensor may be contained in a single housing. In this regard, the sensor, as shown in FIG. 5A, may be positioned within a housing such as the housing 1301 shown in FIG. 13. In some embodiments, the housing may be formed with of a combination of metals, plastics, or other materials. The housing may also include opening for interface connection ports, such as the Analog I/Q connection ports and USB/RS232 connections shown in FIG. 5A. Additionally, the housing may include an area for fitting one or more removable memory modules, such as SD cards, microSD cards, flash, etc. The memory modules may be made accessible by the housing through hinges, doors, latches, etc.

The housing may also include indicators which show the various states of the digital sensor (e.g., in operation, in standby, in an error state, etc.). In some embodiments the indicators may include LEDs, which may blink, change color, or light up based on the state of operation of the digital sensor.

In some embodiments the sensor may be placed within housings of various shapes such as clips, mats, and patches. For example, the digital sensor may be placed into a phone charger. Such a design may minimize the need for running extra wires to or from a power source, such as a smartphone. In another embodiment, the housing may be in the form of a clip for connecting the sensor to objects, such as a bed sheet, shirt, or pants. In another embodiment the sensor may be placed into a mat, which may be positioned next, above, or below a bed. In yet another embodiment, the sensor may be placed into a patch which includes an adhesive, such as tape for connecting the digital sensor directly to an object such as a user.

2.1 Digital Range Gating

In a typical range gated sensor, a continuous RF signal is transmitted into a room. Since the transmitted RF signal is continuous, there is no range gating because the receiver receives most, or all, of the room reflections. In this regard, the continuous RF signal may produce many reflections which may be received by the sensor. Some of the received RF signals will have a static RF signal phase difference with regard to that of the transmitted RF signal, while other received RF signals, such as those which are reflected off moving targets, will contain a changing RF signal phase difference with regard to the transmitted RF signal. As such, "movement information" corresponding to the targets movements, may be determined based on the phase difference between the transmitted RF signal and the received RF signal.

To limit the range of the RF signals received by the receiver of the sensor, the sensor may transmit a pulsed RF signal into a room. During the OFF time (i.e., the time when the pulsed RF signal is not being transmitted,) the RF signals resulting from reflections of the transmitted pulsed RF signal will diminish, and eventually fade away. In some embodiments, the time to for RF signals resulting from the reflections after a transmitted pulsed RF signal has been switched OFF to fade away is about 200 ns (nano seconds).

Upon starting the transmission of an RF pulse at time (t), with a transmission length of T, into a room without any reflected RF signals, the only signals a receiver can receive are reflections from targets within a range of c*(t)/2 where c is the speed of light. For example, 2 ns after an RF pulse is transmitted, the only reflections received at the RF receiver can come from targets within the time of flight of the transmitted RF signal, namely 0.5 ns out and 0.5 ns back. As such, the detectable target range of a 0.5 ns RF pulse may be around 0.1 m.

The introduction of a microcontroller, such as microcontroller 508 into a sensor may allow for more control over the range gating of the sensor. In this regard, the microcontroller 508 may control the timing of transmission and reception of RF pulses. For example, as shown in FIG. 5, to control the transmission of the RF pulses, the microcontroller may send a timing pulse to a pulse generator, such as pulse generator 506. Based on the timing pulse, the pulse generator 506 may send a pulsed repetition frequency (508-PRF) at a rate such as 1 MHz to a switched RF oscillator, such as switched RF oscillator 504. The switched RF oscillator may then transmit, for example, 10.525 GHz. RF pulses at a 1 MHz rate to an antenna feed, such as antenna feed 510 for transmission by an antenna, such as antenna 516.

The ability of the sensor to receive and demodulate signals in a specific time period may also be more readily controlled by microcontroller 508. In this regard, the magnitude detector 512 may be a switched magnitude detector (or any other such mixer) that is switched by the timing control of the microcontroller. The magnitude detector may then receive both the transmitted signal and the received signals as a combined signal according to this timing control. This combined signal from the antenna feed may be demodulated by the mixer to determine a baseband signal, which includes the "movement information." This baseband signal may represent the difference between a) the received signal after the transmitted signal is removed through the demodulation, and b) the transmitted signal.

In this regard, the RF receiver, such as magnitude detector 512, may receive a combined signal of 1) A Sin($\omega$t)+B Sin($\omega$t+phi), where A Sin($\omega$t) is the transmitted RF pulse and B Sin($\omega$t+phi) is the received signal, $\omega$t is the angular frequency at time (t), and phi is the phase of oscillation. Upon the received signal and transmitted signal being input into the magnitude detector, the magnitude detector may combine (i.e., mix) the two signals as follows: 2) [A Sin($\omega$t)+B Sin($\omega$t+phi)] *[A Sin($\omega$t)+B Sin($\omega$t+phi)]. The resulting output is a demodulated signal that may be considered a baseband signal.

In some embodiments an additional magnitude detector(s) may be added to implement two or more receivers. For example, the two receivers may be positioned at a known distance apart (e.g., lambda/8), such that in-phase and quadrature (I/Q) components of a signal may be generated in two signals. Thus, one magnitude detector 512 may produce a single IF signal or baseband signal) that is an in-phase signal. The other magnitude detector may then produce a single IF signal or baseband signal) that is a quadrature phase signal. Post processing of the baseband and IF signals, such as by the IF pre-amplifier 514 and microcontroller 508 may be performed on each of the signals produced by the magnitude detector(s). In some instances each magnitude detector may include a non-linear diode.

The magnitude detector 512 may demodulate the combined signal during the time period it is switched ON by the microcontroller 508 to determine a difference between the transmitted RF pulse signals and the received RF signals (i.e., the movement information), at a certain range. In this regard, the microcontroller 508 may provide range gating control by sending a pulse timing signal to the pulse generator 506, which in turn sends a pulse to cause the magnitude detector to turn on. Continuing the above example, the magnitude detector may turn on at time (t1) for a detection time of T seconds. The range gating may be determined by the time period t1+T, and may produce a range of c*(t1+T)/2. Any reflections after the time period t1+T are not detected, and hence range gating is realised.

2.2 IF Signal and Amplification

In some embodiments the microcontroller may enable the magnitude detector to switch ON for a second period T0 to provide an intermediate frequency amplification stage. As previously discussed, the baseband signal output by the magnitude detector 512 carries the movement signal information. However, the baseband signal may contain natural noise at the low target moving frequencies (e.g., breathing frequencies of 0.2 Hz), commonly referred to as 1/f noise or flicker noise. As such, there may be an undesirable amount of noise added to the baseband signal when it is amplified to a signal level for processing.

The magnitude detector may modulate the baseband signal with an IF signal to bring the low target moving frequencies up to a higher frequency which can be amplified with less noise. In order to create the IF signal, the magnitude detector 512 may demodulate the combined signal during a second time period further controlled by additional timing pulses generated by the microcontroller 508 to determine a difference between the transmitted RF pulse signals and the received RF signals to determine a reference signal. In this regard, the microcontroller 508 may provide additional timing signals to the pulse generator 506, which in turn sends a pulse to cause the magnitude detector to turn on for a second time, prior to, or after, the first time period t1. Continuing the above example, the magnitude detector may turn ON at time (t0) for a detection time of T seconds. In one example, the previously introduced time period (starting at t1) may intentionally target an area of the room where the user's movements were expected to occur, in order to generate a movement signal. In contrast, the targeted range of the newly introduced period (starting at t0) may target a location where not too much movement is anticipated, so as to generate a reference signal. The range gating may be determined by the time period t0+T, and may produce a second range of c*(t0+T)/2. Any reflections after the time period t0+T are not detected during this first ON period. Although the detection time of T seconds is shown as the same for the first and second detections, the detection times may be different. Further, the number of pulses N, which are detected at t0 and t1, may be non-successive pulses, such as every other pulse and the number of pulses detected at t0 and t1 may be different. Further still, t1 and t0 may be measured in the same or different pulses.

The combined signal received by the magnitude detectors from the first and the second time periods may be processed by the microcontroller to determine a baseband reference signal, which is based on the difference between the movement signal and the reference signal.

In one example, in order to modulate the IF signal to a higher frequency, such as 8 kHz, the magnitude detector 512 may:

a. Demodulate the RF pulse at time (t0+T) once every pulse (PRF frequency provided by the pulse generator (i.e., IF Modulation signal in FIG. 5)), and repeating this process 64 times to obtain an average; and b. Demodulate the RF pulse at time (t1+T) once every pulse (PRF frequency), and repeating this process 64 times to obtain an average.

Upon averaging the demodulated pulses N times, then the IF signal frequency may be PRF/2N. Continuing the above example, N may be 64 and PRF may be 1 MHz. As such, the resulting IF frequency may be 8 kHz. The IF signal may be amplified by an IF Preamplifier 514 for amplification prior to signal processing. In this regard, the magnitude detector 512 may pass the IF signals to the IF pre-amplifier which may switch on at 8 kHz, thereby amplifying the 8 kHz IF signal. By amplifying the IF signal at 8 kHz, as opposed to 0.2 Hz, 1/f noise may be mitigated by a factor of 40000, or more or less.

The amplified IF signal may then be forwarded to the microcontroller, which may demodulate the IF signal back to an amplified baseband signal. The baseband signal may then be processed by the microcontroller, as described herein. Thus, with single demodulation timing, such as t1, the sensor may provide range gating, but not IF amplification. With double demodulation timing, such as t0 and t1, the sensor may be capable of providing both range gating and IF stage amplification

2.3 Power

Figure 12:
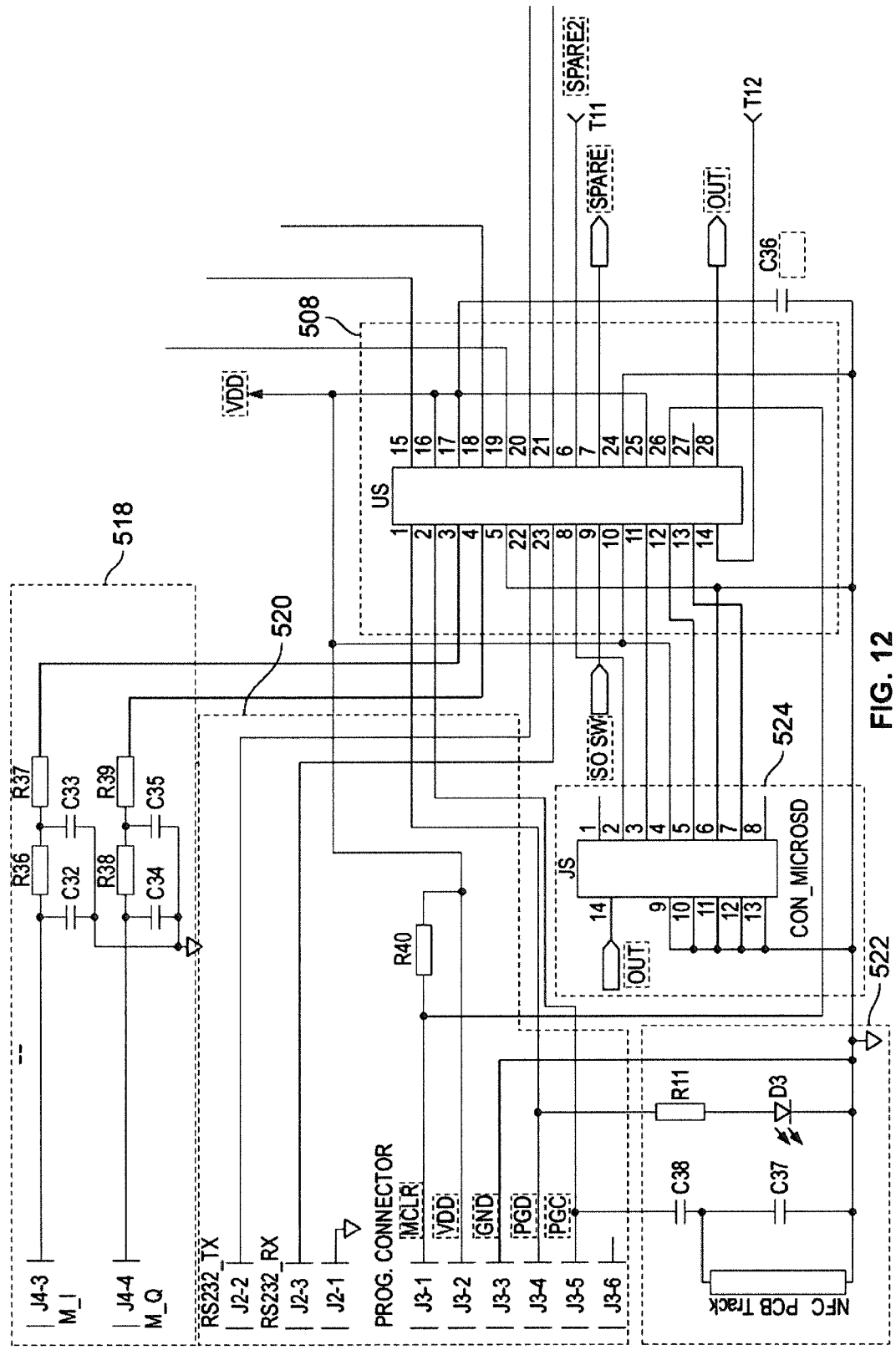
FIG. 12 is a circuit diagram with example components for a microcontroller and outputs suitable for some embodiments of the disclosure.

The digital sensor may be powered from a DC source. In this regard, the digital sensor may be attached to a smartphone via a smartphone adaptor. For example, as illustrated in FIG. 12, the digital sensor may include a micro-USB interface 1208. As such, when the digital sensor is connected to a smartphone via a micro USB-adapter the digital sensor may then receive power, such as 5V to 12V at 2-5 Amps, or more or less.

While only a micro-usb interface is shown in FIG. 12, other interfaces such as USB A-type, USB B-type, mini USB, firewire, thunderbolt, etc. may be possible. Further, other power sources may also be used to power the digital sensor, such as A/C power supplies and/or other DC power supplies. Additionally, no external power source may be necessary, as the digital sensor may include an internal power supply, such as a battery. The battery supply may be charged via external connection or with wireless charging, such as inductive charging.

The power supply may also include power regulation circuit for controlling the power received by the sensor. For example, as illustrated in FIG. 12, a power regulating circuit 1210 may receive power from a source, such as the micro-usb interface 1208 and condition the power into a consistent power value, such as 5V to 12V at 2-5 Amps. Further, the power regulating circuit 1210 may attenuate any power surges.

As illustrated in FIG. 5, the power supply 502 may be used to power the components included within box 503. In this regard, the power supply may be directly connected to the switched RF oscillator, 504, pulse generator 506, microcontroller 508, magnitude detector 512, IF pre-amplifier 514, analog interface 518, USB/RS232 520, NFC 522, and memory 524. In some embodiments the power supply In addition, the power supply may be used to power other components such as powered antenna feeds, amplifiers, etc.

2.4 Pulse Generator

The pulse generator circuit 506 receives a PRF timing signal, as shown in FIG. 5, from the microcontroller 508. Upon receiving the PRF timing signal the pulse generator may generate a PRF signal, such as a 1 MHz pulse with a 0.5 microsecond duration every 1 microsecond, or more or less. An example illustration of a PRF timing signal is illustrated as signal 408-PRF in FIG. 4.

In addition, the pulse generator 506 may receive an IF timing pulse signal from the microcontroller 508, and generate an IF modulation pulse signals. Upon receiving the IF timing pulse from the microcontroller 508, the pulse generator may send IF modulation pulse signals to the magnitude detector 512. As described previously, the pulse generator may send IF modulation pulses to each receiver in the magnitude detector. For example, the pulse generator may send an IF modulation pulse to an in-phase receiver and a quadrature receiver.

Figure 9:
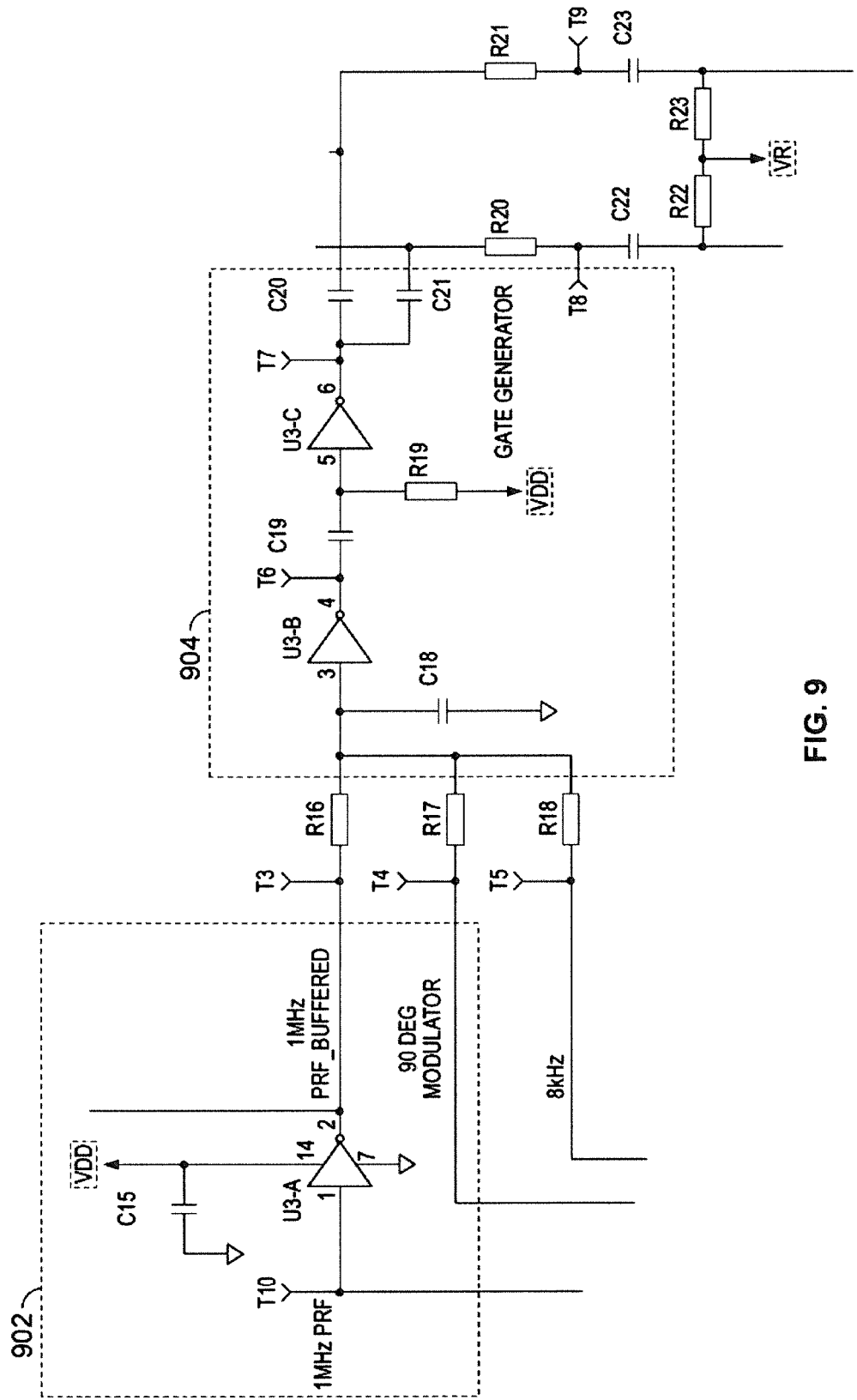
FIG. 9 is a circuit diagram with example components for a pulse generation circuit suitable for some embodiments of the disclosure.
Figure 10:
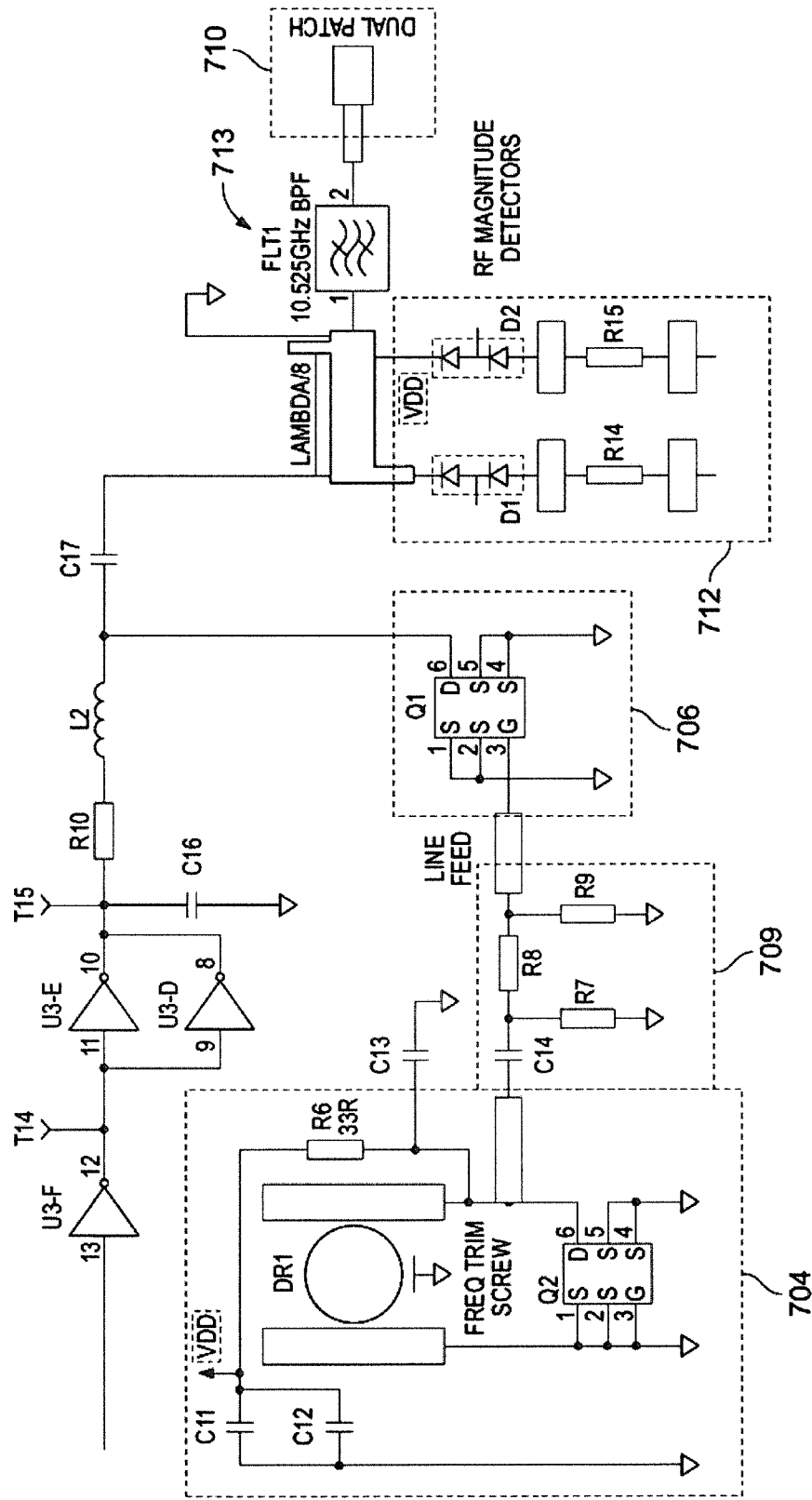
FIG. 10 is a circuit diagram with example components for a RF transmission circuit.

A representation of an example circuit for implementing the pulse generator is found in FIG. 9. The pulse generator may include a buffer 902 and a gate generator 904. The buffer 902 assures proper signal voltage (polarity) is delivered to the gate generator 904. The gate generator 904 may include two or more inverters and may generate the IF modulation timing pulses for the magnitude detectors.

2.5 Switched Oscillator

The PRF timing signal may cause a switched RF oscillator, such as oscillator 504, to switch on and off, thereby causing the switched RF oscillator to transmit RF pulse signals. In this regard, the RF oscillator may operate at 10.525 GHz, and be pulsed (i.e., turned on and off) at the 1 MHz PRF rate. The output signal of switched oscillation circuit 406 is the RF pulse signal illustrated as signal 406-RFPS in FIG. 4 and "RF Tx" in FIG. 5.

The RF pulse signal may be transmitted to an antenna feed 510, where the RF pulse signal may be output via an antenna 516 at a duration of 0.5 microseconds every 1 microsecond, or more or less. Such an RF pulse train with this characteristic may have a narrow signal bandwidth (e.g., approximately 25 MHz) and may be suitable for range gating applications and/or meeting RF regulatory approval certification. RF signals, such as those which are reflected off moving targets, may be received by the antenna 516 and sent from the antenna feed 510, to a magnitude detector 512.

2.6 Magnitude Detector

In one example, the magnitude detector 512 will actually include two magnitude detectors processing the combined transmitted and reflected signals at a lambda/8 spacing, as indicated in FIG. 5. The magnitude detector may act as a mixer and demodulate the combined transmitted RF signal and received RF signals so as to extract the phase difference between the receive signal and the transmit signal. Further, the magnitude detector may utilise its switching capability to generate an IF signal from the demodulated RF signal to mitigate the 1/f noise, as previously described.

Both the transmitted RF signal and received RF signals, such as those which are reflected off moving targets, may be presented to the input of a RF magnitude detector 512 (e.g., a homodyning receiver peak detector) as a combined signal. The magnitude detector 512 may operate as a receiver, which may generate a measure of the magnitude and/or phase of the received signals with respect to the transmitted signal. The phase and/or magnitude of the received signal may change with respect to the transmitted signal when the target moves. As result, the magnitude detector 512 may determine a measure of the movement of a target based upon the phase difference between the transmitted and reflected signals.

The magnitude detector receiver may be switched on and off at offset times "t1" from the start time of the RF pulse. For instance, the microcontroller 508 may provide range gating control by sending a pulse timing signal to the pulse generator 506, which in turn sends a pulse to cause the magnitude detector to turn on. Additionally, the magnitude detector may receive the transmitted RF pulse. As such, the magnitude detector may receive both the transmitted signal and the received signals as a combined signal during the time the magnitude detector is on. This combined signal may be demodulated to determine a baseband signal, which includes the "movement information." In this regard, the difference between the received signals provides a measure of the movement that has occurred in the time period from the start of the RF pulse, and hence the movement that has occurred within the range (c*t1)/2, where c is the speed of the light. The baseband signal may be the difference between a) the received signal after the transmitted signal is removed through the demodulation, and b) the transmitted signal.

Continuing the above example and as previously described, the magnitude detector may turn on for a period T1 at time t1, for the purpose of range gating. The magnitude detector may also turn on for a second period T0 at time t0, to provide an intermediate frequency amplification stage. As previously discussed, the signal output by the magnitude detector 512 carries the movement signal information, as well as 1/f noise. As such, the magnitude detector may modulate the signal with an IF signal to bring the low target moving frequencies up to a higher frequency which can be amplified with less noise.

In order to create the IF signal, the magnitude detector 512 may demodulate the combined (transmitted+reflected) signal during a second time period further controlled by additional timing pulses generated by the microcontroller 508 to determine a difference between the transmitted RF pulse signals and the received RF signals to determine a reference signal. The difference between movement signal and the reference signal is the IF signal. The IF signal may then be modulated to a higher frequency, such as 8 kHz, as previously described.

Referring back to the use of two magnitude detectors, this is done too overcome nulls in movement sensitivity that may occur every λ/2 in space, where λ is the wavelength of the RF signal, a second "quadrature phase" peak detector receiver may be placed at a λ/8 distance from the first "in phase" receiver. For example, in the case of a 10.525 GHz frequency RF signal, the distance λ/8 is 3.55 mm. The physical spacing of this second receive circuit generates a quadrature receiver output which has maximum movement sensitivity at the point of the "in phase" minimum sensitivity.

2.7 IF Pre-Amplifier

The received in phase and quadrature phase IF signals may then be processed through an IF Pre-amplifier 514. The IF pre-amplifier 514 may amplify both the in phase and quadrature phase IF signals separately. The amplified signals may then be passed onto the microcontroller 508 for sampling and digital processing, such as digital demodulation and baseband digital filtering.

Figure 11:
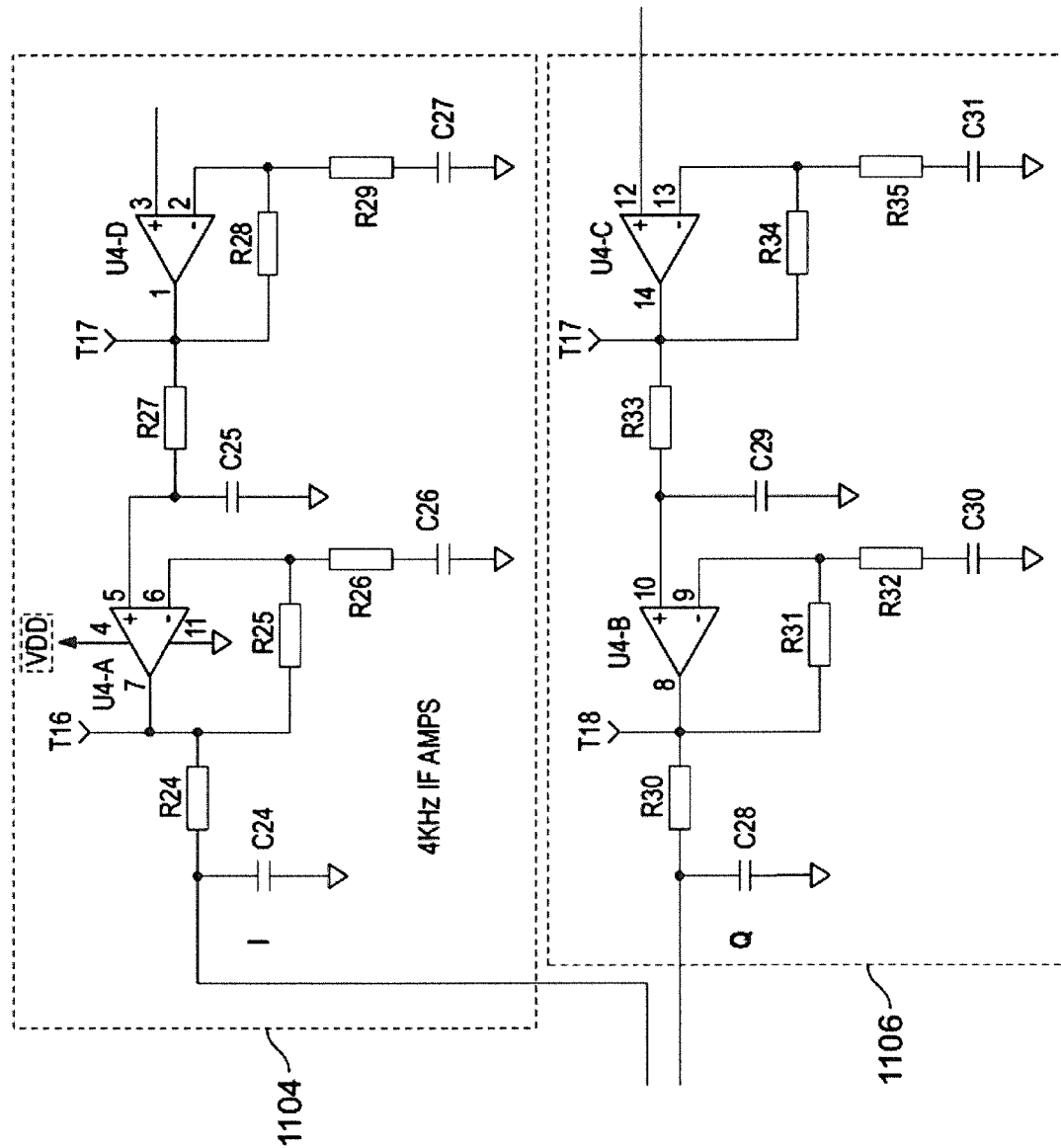
FIG. 11 is a circuit diagram with example components for an IF pre-amplifier circuit suitable for some embodiments of the disclosure.

As shown in FIG. 11, the IF pre-amplifier may include two separate channels. An in phase channel 1104 and a quadrature phase channel 1106. As further illustrated in FIG. 11, each phase channel includes two amplification stages, though variations in the number of stages are possible. For example, each channel may include one, two, three, four, etc., amplification stages. Additionally, the channels may include a different number of amplification stages.

2.8 Microcontroller

In addition to providing the timing signals, as described previously, the microcontroller or microprocessor may also demodulate the amplified IF signals and process the resulting amplified baseband signals. In this regard the microcontrollers firmware may be programmed with certain digital signal processing "DSP" capabilities. For example, the microcontroller may be programmed to receive and sample the amplified signals at 128 kbps with 2048 times oversampling, or more or less, each with an analogue to digital (ADC) converter. In some embodiments the ADC may use 10 bits, or more or less. The microcontroller may be programmed to detect the difference between the reference signal and the movement signal that exists in both the in phase signal and the quadrature phase signal. As result, the microprocessor synchronously demodulates the amplified IF modulated receive signals (I and Q) and produces amplified baseband signals.

The resulting demodulated signals (I and Q) may then be filtered by algorithms within the microcontroller. In this regard, the microprocessor may filter the digital baseband signals. For example, the microcontroller 616 may be programmed to perform the bandpass filtering of out of band interfering signals and low harmonic emissions from the sensor. The circuit may also generate separate outputs for respiration and movement since movement and respiration signals are at different frequencies and may be filtered by different filters. As the microcontroller 508 provides the timing of the pulse generator 506, including the PRF and IF timing signals, the microcontroller is aware of the time signals are sent and received. Accordingly, the microcontroller can demodulate both the in phase and quadrature phase signals.

With such operations, an example pulsed RF range gated motion sensor with a narrow signal bandwidth may be implemented.

The microcontroller may be a single integrated chip including a processor core, memory, and programmable input/output peripherals.

3. Digital Sensor Embodiments

Figure 6:
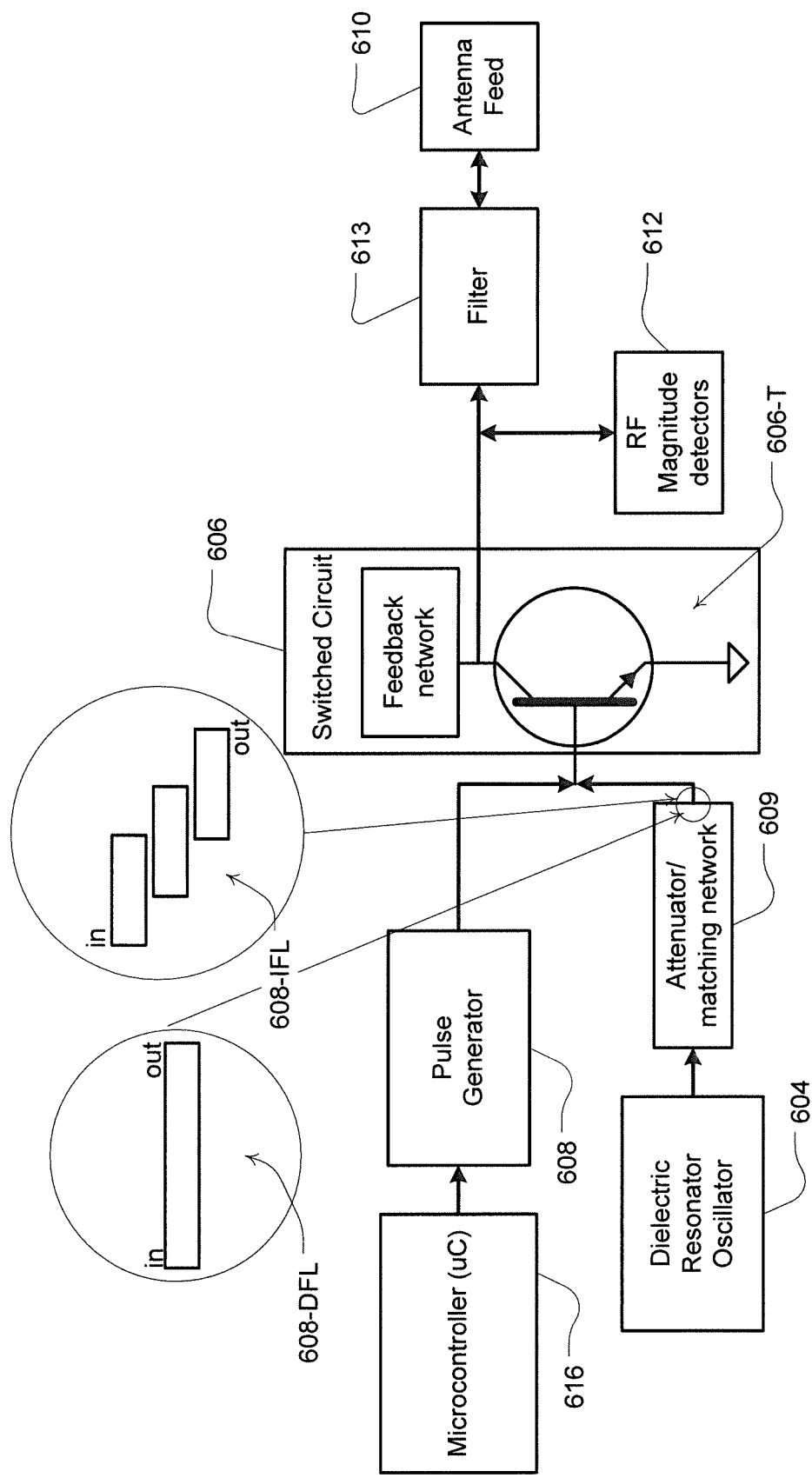
FIG. 6 is a block diagram with example components for an injection locking embodiment of the switched oscillator of FIG. 4.

An example embodiment of a frontend section for implementing this range gated pulsed radar system may be considered in reference to the circuit component diagram of FIG. 6. In this embodiment, the switched wideband RF oscillator 606 is implemented. Typically, a wideband oscillator can be prone to frequency stability issues, such as that caused by humidity and/or temperature variations, component and batch parasitic variations and housing proximity effects. However, the present circuit design permits the oscillator to maintain the RF centre frequency within desired limits (e.g., within approximately 10 MHz of 10.525 GHz). It provides fast switching and a stable pulsed RF signal. It permits a fast turn on of the oscillation circuit while providing a fast stabilisation of frequency and amplitude. The turn on time Δt is related to Q and hence bandwidth (BW) of the oscillator may be as follows:

$$\Delta t = Q/(nf_0) \sim 1/BW.$$

In some cases, the oscillation circuit may optionally be hermetically sealed and/or may optionally include a temperature control circuit.

The oscillator 606 may be injection locked by the DRO oscillator 604. Injection locking occurs when the wideband oscillator 606 is disturbed by the DRO oscillator 604 operating at a nearby frequency. Since the coupling is strong enough and the frequencies near enough, the DRO oscillator can capture the wideband oscillator, causing it to have essentially identical frequency as the DRO oscillator. Thus, in a typical embodiment, these two oscillators have a suitable "lock in range" for injection locking.

In the circuit variant of FIG. 6, a high stability Dielectric Resonator Oscillator, DRO, circuit may include a transistor (not shown), such as a low noise gallium arsenide (GaAs) Field Effect Transistor (FET) or a Bipolar Junction Transistor (BJT), configured as an amplifier with feedback provided via a frequency stable Dielectric Resonator coupled with microstrip lines to the gate (base) and drain (collector) circuits of this transistor. Such a DRO oscillator, operating at for example, 10.525 GHz, may be implemented for the frequency reference for the radar system centre frequency.

This DRO reference oscillator is configured to maintain the working centre frequency of the sensor within a regulatory specification over the operating temperature and humidity range of the product. This reference oscillator circuit may be enclosed inside a metal cavity to ensure good screening and high quality factor. Also, fine tuning of the centre frequency may optionally be provided by a mechanical tuning screw in a top of a screen above the resonator.

The output signal from the DRO reference oscillator 604 may be fed into the switched wideband oscillator 606 via an attenuator and/or matching network 609 having a feed line to the switched oscillator 606. The attenuator and matching network properties may be configured to ensure that the second oscillator will only oscillate at a frequency determined by the reference oscillator over the working temperature and humidity range of the product. The configuration of the attenuator may set the injection level to the modulated oscillator 606 and hence the capture frequency range. The matching network may be configured to convert the low impedance output of the reference oscillator 604 to higher impedance suitable for injection into the modulated oscillator 606. The matching network may be a shunt-open-circuited-stub:transmission-line:shunt-open-circuited-stub directly coupled network. The feedline from the network 609 may be coupled to the gate (base) of the transistor 606-T. In some embodiments, this microstrip feedline to the transistor may be low-pass, such as when it is formed in a direct feed 608-DFL configuration. However, in some embodiments, the feed line may be high-pass, such as when it is formed in an indirect feed configuration 608-IFL.

Thus, the switched oscillator 606 may include a transistor 606-T, such as an FET. This transistor may be configured with a tuned microstrip feedback network, which, in addition to any desired gain characteristics, will include any desired oscillation characteristics suitable for the lock in range. Some or all of the feedback may be provided by the internal parasitics of the transistor 606-T. This tuned microstrip feedback network may be configured to ensure fast rise and fall time of the output signal required for range gating of the pulse radar system. For example, such range gating of the pulse radar system may be implemented in accordance with the methodologies disclosed in U.S. Patent Application Publ. No. 2015-0216424, the entire disclosure of which is incorporated herein by reference.

The bias circuit of the switched oscillator 606 is also supplied by a pulse from the pulse generator 608 so that oscillations can only occur during the application of the switch pulse. As illustrated in FIG. 6, this output of the pulse generator is also input to the gate or base of the transistor 606-T of the switched oscillator 606. The pulse generator may be controlled with timing signals from the microcontroller 616. As such, the microcontroller 616 may be able to store timing information on the transmitted and received signals.

The switched oscillator then produces an RF pulse at the stable reference frequency when a positive pulse is applied to the base circuit by the pulse timing circuit or pulse generator that is responsive to the microcontroller. In some versions, the pulse generator may include a fast logic gate (e.g., a NAND gate or AND gate circuit) to generate the timing pulse. Optionally, the output of the logic gate may be applied to a circuit network configured to maintain a wideband characteristic to ensure fast and effective switching of the switched oscillator.

The pulsed RF frequency output from the switched oscillator 606 is then input to the peak/magnitude detectors 612 and filter(s) 613. Optionally, this pulsed RF frequency output may be input to these components via a series resistor or via an attenuator network. The series resistor can be implemented to optimise the drive level to the magnitude detectors, isolate the switched oscillator from signal reflections and improve system impedance match.

The filter 613 may be implemented with a microstrip bandpass filter and connected to the antenna feed 610. The microstrip bandpass filter may be implemented to ensure high rejection of out of band interfering signals and low harmonic emissions from the sensor. This filter may provide high rejection at radio/TV broadcast, Wi-Fi, DECT, ISM and mobile phone frequencies commonly encountered in domestic and clinical environments. The filter may also provide sufficiently high rejection at the second harmonic frequency (e.g., 21.05 GHz in the case of a 10.525 GHz oscillator) to ensure regulatory product compliance in all world markets. The filter may be a high performance sub-miniature energy-trapping low insertion loss coupled H resonator bandpass filter in some embodiments.

The magnitude detectors 612 can be implemented to provide two phase separated receive I & Q channel IF signals that are proportional to the magnitude sum of the forward propagating and reverse propagating radar signals. In this regard, the inputs to each magnitude detector may be separated along a microstrip feed line by a distance of $\lambda/8$ as previously discussed. However, in any of the embodiments described herein, the separation distance may be different. For example, the I & Q magnitude detector separation distance may be generalized to $+/-(2n-1)\lambda/8$. Thus, the separation distance may optionally be chosen according to any of the following distances: $\lambda/8, 3\lambda/8, 5\lambda/8, 7\lambda/8, \ldots$, etc.

Figure 7:
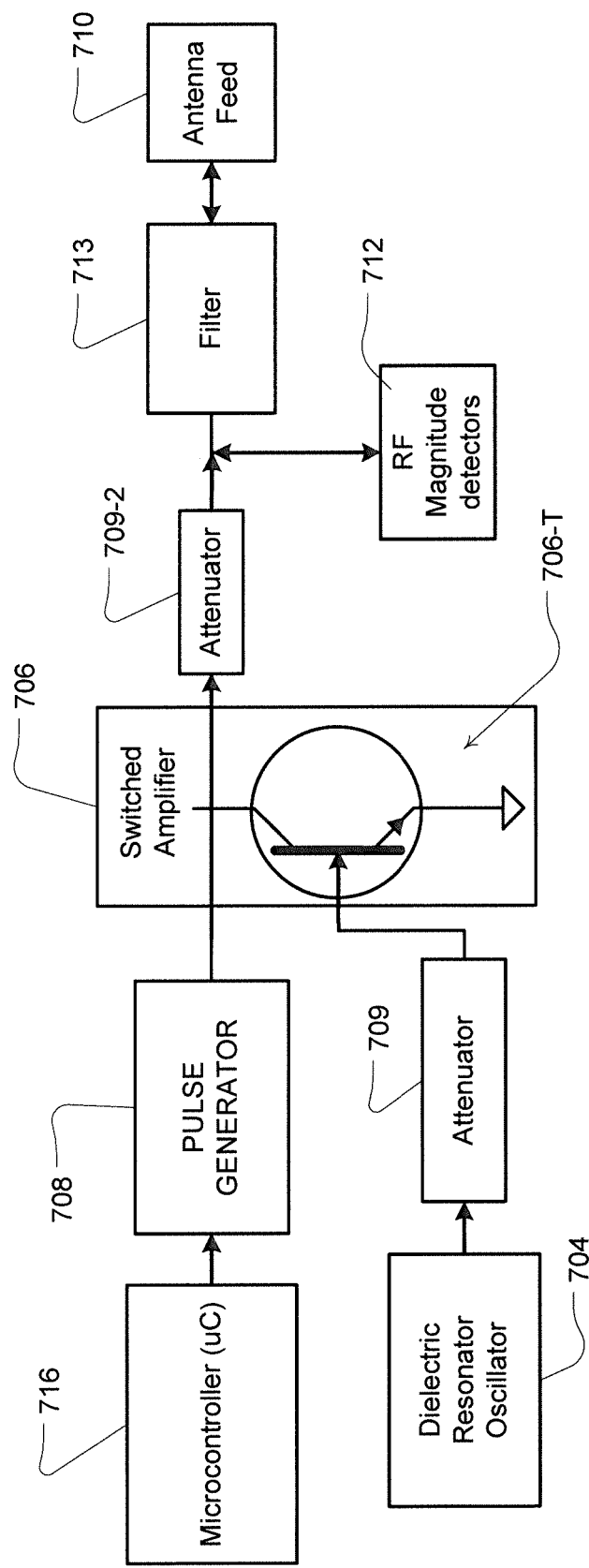
FIG. 7 is a block diagram with example components for an amplifier embodiment of the switched oscillator of FIG. 4.
Figure 8:
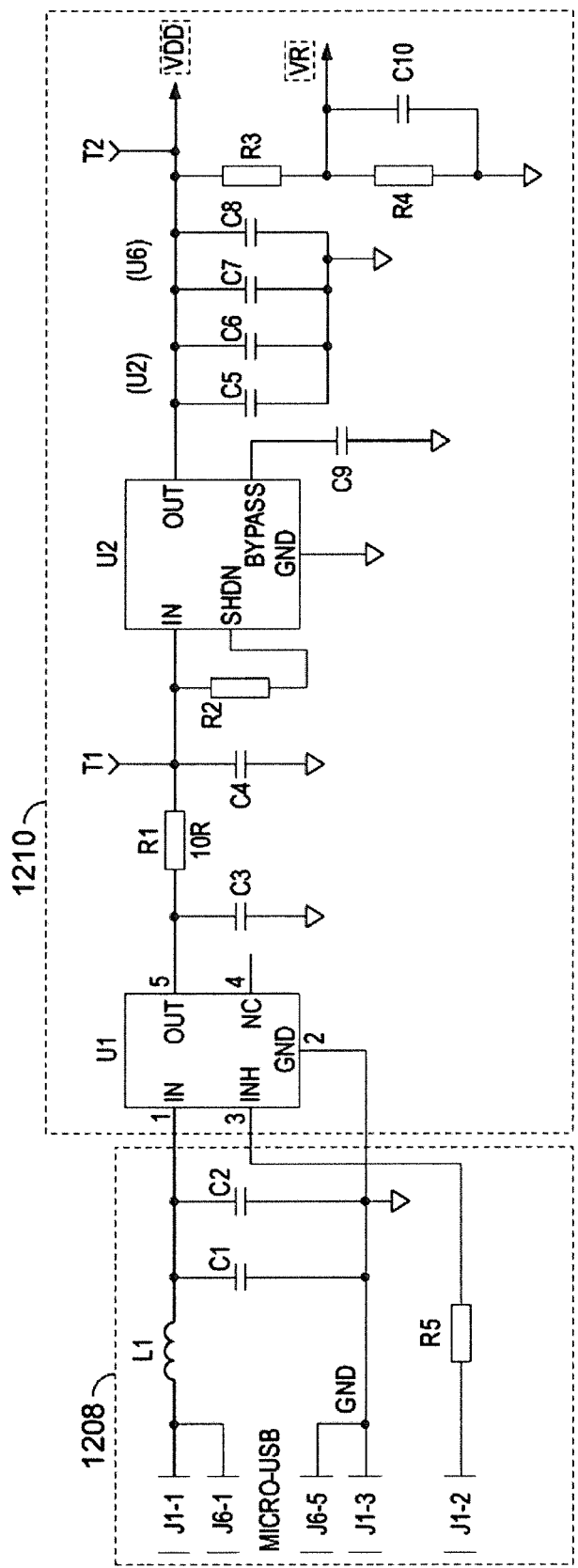
FIG. 8 is a circuit diagram with example components for a power regulation circuit suitable for some embodiments of the disclosure.

Alternative embodiments of the present technology in which the switched oscillation circuit is provided in an amplification configuration may be considered in view of the illustrations of FIG. 7. This embodiment is similar to that of the embodiment of FIG. 6. However, in this embodiment, rather than having a switched oscillator 606, the circuit employs a switched wideband amplifier 706. In the examples, the amplifier is implemented in a common source configuration. However, alternative configurations may be implemented in some embodiments (e.g., common drain or common gate.)

In this circuit variant, the high stability dielectric resonator oscillator 704 and the pulse generator 708 may employ the configuration discussed with regard to the embodiment of FIG. 6. The output signal from the DRO reference oscillator 704 is input to attenuator 709. The attenuator ensures frequency stable operation of the reference oscillator under all conditions and is configured to apply an optimum drive level to the switched amplifier 706. Like the embodiment of FIG. 6, the pulse generator 708 may be controlled by timing pulses from the microcontroller 716.

The outputs of the attenuator 709 and the pulse generator 708 are coupled to the switched RF power amplifier 706. In this regard, the switched power amplifier may include a transistor 706-T, such as an FET. The pulse switching signal from the pulse generator is applied to the drain (collector) of the transistor 706-T. The attenuated signal from the DRO oscillator 704 is applied to the gate (base) of the transistor 706-T. The source (emitter) of the transistor 706-T may be coupled to a ground, such as a ground plane of a printed circuit board (PCB) on which the circuit is formed.

The switched power amplifier thereby produces an amplified radar pulse at the stable reference frequency (e.g., 10.525 GHz) when a positive pulse is applied to the drain (collector) by the timing of the pulse generator circuit as controlled by the microcontroller, which may include circuit components, such as series resistor, series inductor and capacitors, configured to ensure fast switching and minimal overshoot of the modulation pulse applied to the modulated amplifier 706.

The pulsed radio frequency output from the modulated power amplifier 706 is fed via an optional second attenuator 709-2, through the magnitude detectors 712, through filter 713 (e.g., bandpass filter as previously described in reference to FIG. 6) to the sensor antenna (such as a horn probe antenna) or antenna feed 710. The second attenuator 709-2 may be configured to optimise the drive level to the magnitude detectors and improve system impedance match. This second attenuator can be omitted in some embodiments.

Some potential advantages of the circuit configuration of FIG. 7 may include the elimination of the lock in range requirements. Additionally, the circuit complexity associated with implementation of a wideband oscillator is removed. Moreover, the turn on time of the wideband RF amplifier can be faster than the wideband RF oscillator. With the use of the microcontroller, filtering requirements may be handled digitally, reducing the power consumption and size of the sensor.

4. Microcontroller

The microcontroller 508, in addition to implementing the digital baseband filtering functions and RF transmission timing functions as discussed herein, may also be programmed to run an integrated engine. The integrated engine may enable the microcontroller to manage operations of the digital sensor. In this regard, the microcontroller may be used to trigger sensor operation by, for example, starting, stopping, and/or pausing sensing operations of the sensor. Further, the microcontroller may also be programmed to control the power state of the sensor, such powering on/off the sensor and placing the sensor into standby. As previously discussed, the microprocessor may also be programmed to vary the range of the sensor.

The microcontroller 508 may also be programmed to manage the user's physiological data which is received. In this regard the received signal data may be time and/or date stamped using information from an external source, such as a smart phone. Alternatively, the sensor may include an internal clock. The received signal data may be stamped by the microcontroller or upon output from the microcontroller to an external device, such as a smart phone. The stamped data may then be displayed, stored and/or output from the digital sensor.

The signal data may be organized into thirty second epochs, or more or less, which include various physiological measurements of the user such as motion, sleep, respiration and/or heartbeat data. In this regard, the microcontroller, upon processing the received signal as discussed herein, may process the data into small subsets representative of user physiology. For example, such movement detection algorithms may be implemented in accordance with the methodologies disclosed in any of U.S. Patent Application Publ. No. 2009/0203972, mentioned previously, International Patent Application No. PCT/US14/045814, the entire disclosures of which are each incorporated herein by reference.

The received signal data may be stored within memory in the digital sensor, such as the memory accessed by the microcontroller. As illustrated in FIG. 12, the microcontroller 508 may be connected to memory 524. As previously explained, the memory 524 may include SD cards, microSD cards, flash, etc. While the memory is illustrated as being separate from the microcontroller in FIG. 12, the memory 524 may be integrated into the microcontroller. The data may be logged into the memory at a speed of 64 bps, or more or less, depending on the type of memory. The amount of data stored may be dependent upon the size of the memory used in the digital sensor. For example, the memory 524 may save 12 hours or 24 hours of user data.

Optionally, the microcontroller 508 may also be programmed to detect physiological data based on processing of the motion signals (e.g., respiration and/or cardiac signals). For example, it may be programmed to generate data such as time to sleep, sleep duration, time of sleep states, absent sections, unknown section, efficiency scores and/or other detected information, such as detected sleep disordered breathing event scores (e.g., an Apnea/hypopnea count (AHI)). Such data generation may be implemented in accordance with the methodologies disclosed in U.S. Patent Application Publ. No. 2016/0151603, the entire disclosure of which is incorporated herein by reference.

The microcontroller 508 may also control the output of data. As illustrated in FIG. 12, the microcontroller may be connected to an NFC transceiver device, such as an NFC card emulator 522 which can be read by an external device such as a smartphone at 212 kbps, or more or less. While an NFC device is discussed, other technologies may also be implemented such as LTE, Wi-Fi and Bluetooth. The NFC card emulator 522 may also contain data which, when being read by a device, causes the device to launch an application (s) which reads the data from the memory 524 of the sensor. In this regard, the external device may 'tap' the sensor to read the NFC card emulator 522, thereby causing the application to launch on the external device.

Upon launching the application, the external device may retrieve a user's physiological data, from a certain period of time, such as 24 hours, or other amounts of time stored in the memory. In this regard, the NFC card emulator 522 may retrieve data from the memory 524, assisted by instructions from the microcontroller 508. In some embodiments, the retrieved data may be automatically backed up into the application and/or onto a separate cloud server.

As illustrated in FIG. 13, the retrieved data may then be displayed on a display of the external device. The display may summarize the data which is received by the external device, such as data obtained while a user slept. In the example illustrated in FIG. 13, data such as time to sleep, sleep duration, time of sleep states, absent sections, unknown section, etc., may be displayed in graph and/or chart form. Additionally, the external device may determine and/or display sleep, or other condition related data such as sleep stages related data, sleep efficiency scores and/or other detected information, such as detected sleep disordered breathing event scores, e.g., (AHI) received from the microcontroller. However, in some cases, the smart phone may itself obtain such information simply by receiving and processing the raw motion signal (e.g., I/Q signals) from the sensor.

The sensor may also include other digital outputs. In this regard, the sensor may include outputs such as RS232, serial, USB, etc. Output via the digital outputs may occur at 64 bps and include a 50 μV signal resolution. External devices connected to these digital outputs may receive data and otherwise function as outlined above in regard to the NFC connection. In addition the digital outputs may provide raw I/Q data for external processing or storage.

The digital sensor may also include analogue outputs. For example, the microcontroller may be configured to generate analogue I/Q sensor signals by converting the digital I/Q signals into respective analogue signals using a digital to analogue converter (DAC). The DAC may be a 10 bit DAC, or more or less. The analogue IQ signal may then be passed via the analogue outputs. The analogue outputs may pass the analogue signals at a set bit rate a set bit width modulation, such as 64 bps utilising 10 bit pulse width modulation (PWM). Thus, the sensor may then output the re-generated analog I/Q signals, each representing a raw motion signal from the sensor.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive. It will further be understood that any reference herein to subject matter known in the field does not, unless the contrary indication appears, constitute an admission that such subject matter is commonly known by those skilled in the art to which the present technology relates.

The invention claimed is:

1. A digital radio frequency motion sensor comprising:
a radio frequency transmitter, the transmitter configured to emit radio frequency pulses; and
a receiver configured to receive reflected ones of the emitted radio frequency pulses,
the radio frequency transmitter comprising:
a microcontroller configured to generate timing pulses;
a pulse generator configured to generate signal pulses in response to the timing pulses;
an oscillator configured to generate a stable radio frequency oscillating signal; and
a switched circuit coupled to the pulse generator and the oscillator, the switch circuit configured to generate a pulsed radio frequency oscillating signal whose frequency is derived from the oscillator; and
wherein the microcontroller is configured to control at least one of:
demodulating a combined signal of emitted and received signals to determine a baseband signal, and modulating the baseband signal to produce an intermediate frequency (IF) signal at the receiver,
digital demodulation of an intermediate frequency (IF) signal after a stage of IF signal amplification to produce a baseband signal at the receiver,
digital amplification of one or more baseband signals from the receiver, and
digital filtering of one or more signals or baseband signals from the receiver.

2. The sensor of claim 1 wherein the oscillator comprises a dielectric resonator.

3. The sensor of claim 1 wherein the pulse generator comprises a logic gate circuit configured to receive a timing signal generated by the microcontroller.

4. The sensor of claim 1 wherein the microcontroller is coupled with the receiver to sample a signal from the receiver representing phase and/or magnitude differences between the received reflected ones of the emitted radio frequency pulses and the emitted radio frequency pulses.

5. The sensor of claim 1 wherein the microcontroller is configured to digitally demodulate the signal from the receiver.

6. The sensor of claim 1 wherein the receiver generates in phase and quadrature phase signals for sampling at inputs to the microcontroller.

7. The sensor of claim 1 wherein the receiver comprises a mixer, wherein the microcontroller controls timing of the mixer's operation.

8. The sensor of claim 7 wherein the mixer comprises a switched magnitude detector.

9. The sensor of claim 1 wherein the microcontroller is configured to generate an indicator of any one or more of respiration, sleep and heart rate information from one or more digitally demodulated signals from the receiver.

10. The sensor of claim 1, wherein the microcontroller triggers sensor operation by turning the sensor on and off.

11. The sensor of any of claim 1, wherein the microcontroller is configured to control storing of data from received signals in epochs.

12. The sensor of claim 11, further comprising a memory, wherein the memory stores the epochs.

13. The sensor of claim 12, wherein the memory comprises one or more of SD cards, microSD cards, and flash.

14. The sensor of claim 12 wherein the memory is integrated into the microcontroller.

15. The sensor of claim 1 wherein the sensor is configured for wireless transmission from the sensor of data derived from received signals.

16. The sensor of claim 15, where the wireless transmission comprises NFC communications.

17. The sensor of claim 1 further comprising a digital or analogue output connection.

18. The sensor of claim 17, wherein the digital or analogue output connection is a RS232, serial or USB connection.

19. The sensor of claim 1 wherein the sensor comprises an analog output, and wherein the microcontroller is configured to convert digital signals received from the receiver into analogue signals for output via the analog output.

20. The sensor claim 19 wherein the analog signals comprise a pulse width modulated signal.

21. The sensor of claim 1 further comprising a housing, wherein the sensor is contained within the housing.

22. The sensor of claim 1 wherein the transmitter and receiver comprise a single printed circuit board and wherein the microcontroller is a chip coupled to the single printed circuit board.

23. The sensor of claim 1 wherein the receiver comprises two detectors for mixing the emitted radio frequency (RF) pulses and the received reflected ones of the emitted radio frequency pulses, the two detectors including one magnitude detector for in-phase signals and one magnitude detector for quadrature phase signals, wherein each magnitude detector is configured to switch on, at a first defined point in time t1 and for a first defined time duration T1 within each one of a first number of RF pulses, to effect range gating capability of the sensor.

24. The sensor of claim 23, wherein each detector is switched at a second defined point in time t0 for a second defined time duration T0 within each one of a second number of RF pulses, the first defined point in time t1 being different from the second defined point in time t0; and wherein each detector modulates the mixed pulses at an intermediate frequency that is higher than a baseband frequency.

25. The sensor of claim 24, wherein the first number of RF pulses is equal to the second number of RF pulses.

26. The sensor of claim 24, wherein at least the first or the second number of RF pulses is a number of consecutive pulses.

27. The sensor of claim 24, wherein each detector alternates between being switched on at the first defined point in time t1, during the first number of RF pulses, and being switched on at the second defined point in time t0, during the second number of RF pulses.

28. The sensor of claim 24, wherein first time duration T1 is equal to second time duration T0.

29. The sensor of claim 24, wherein first defined time t1 is different from the second defined time t0.

30. The sensor of claim 23, wherein the detectors are magnitude detectors.

31. The sensor of claim 24, wherein the receiver further comprises, for each detector, a pre-amplifier or an amplifier for amplifying the modulated mixed pulses at the intermediate frequency.

32. The sensor of claim 31, wherein the microcontroller is further configured to demodulate the amplified modulated mixed pulses into baseband signals.

33. The sensor of claim 1, wherein the receiver and radio frequency transmitter are digitally controlled by the microcontroller, to automate changing of at least some of their parameters.

34. A circuit for generating signals to produce radio frequency pulses for range gated physiology sensing, the circuit comprising:
   a microcontroller configured to generate timing pulses;
   a pulse generator configured to generate signal pulses in response to receiving the timing pulses;
   an oscillator configured to generate a radio frequency oscillating signal;
   a switched circuit coupled to the pulse generator and the oscillator, the switched circuit configured to generate a pulsed radio frequency oscillating signal in accordance with the signal pulses and radio frequency oscillating signal; and
   an antenna feed coupled with an output of the switched circuit to accept the pulsed radio frequency oscillating signal and emit radio frequency pulses in accordance with the pulsed radio frequency oscillating signal via an antenna, the antenna feed configured to receive reflected ones of the emitted radio frequency pulses; and
   wherein the microcontroller is configured to control at least two of:
   demodulating a combined signal of emitted and received signals to determine a baseband signal, and modulating the baseband signal to produce an intermediate frequency (IF) signal,
   digital demodulation of an intermediate frequency (IF) signal after a stage of IF signal amplification to produce a baseband signal,
   digital amplification of one or more baseband signals derived from the received reflected ones of the emitted radio frequency pulses, and
   digital filtering of one or more signals or baseband signals derived from the received reflected ones of the emitted radio frequency pulses.

35. The circuit of claim 34 further comprising a set of magnitude detectors coupled with the antenna feed, wherein the set of magnitude detectors detect signals received with the antenna feed based on signals generated from the switched circuit.

36. The circuit of claim 35 wherein microcontroller is configured to sample one or more outputs of the magnitude detectors.

37. The circuit of claim 35 wherein outputs of the set of magnitude detectors comprise an in phase signal and a quadrature phase signal representing phase and/or magnitude differences between the received reflected ones of the emitted radio frequency pulses and the emitted radio frequency pulses.

38. The circuit of claim 35 wherein the microcontroller is configured to digitally demodulate outputs of the set of magnitude detectors.

39. The circuit of claim 35 wherein the microcontroller is configured to digitally filter outputs of the set of magnitude detectors.

40. The circuit of claim 35 wherein the set of magnitude detectors derive the one or more baseband signals that are digitally filtered by the microcontroller.

41. The circuit of claim 35 wherein the set of magnitude detectors derive the one or more baseband signals that are digitally amplified by the microcontroller.

42. The circuit of claim 34 wherein the oscillator comprises a dielectric resonator.

43. The circuit of claim 34 wherein the pulse generator comprises a logic gate circuit configured to receive a timing signal generated by the microcontroller.

44. The circuit of claim 34 wherein the microcontroller is configured to generate one or more of respiration, sleep and heart rate information based on one or more signals received via the antenna feed.

45. The circuit of claim 34, wherein the microcontroller is configured to trigger the circuit's sensing operations by selectively turning transmissions on and off.

46. The circuit of claim 34, wherein the microcontroller is configured to control storing of data from received signals in epochs.

47. The circuit of claim 34, further comprising a memory interface.

48. The circuit of claim 34 wherein the circuit includes a wireless transceiver for wireless transmission of data derived from sensing signals.

49. The circuit of claim 34 further comprising a digital or analogue output connection.

50. The circuit of claim 34 wherein the circuit comprises an analog output, and wherein the microcontroller is configured to convert digital signals sensed by the circuit into analogue signals for output via the analog output.

51. The circuit of claim 50 wherein the analog signals comprise a pulse width modulated signal.

52. The circuit of claim 34 wherein the circuit comprises a single printed circuit board and wherein the microcontroller is a chip affixed to the single printed circuit board.

53. The sensor of claim 1 wherein the microcontroller is configured to control demodulating a combined signal of emitted and received signals to determine a baseband signal, and modulating the baseband signal to produce an intermediate frequency (IF) signal.

54. The sensor of claim 1 wherein the microcontroller is configured to control digital demodulation of an intermediate frequency (IF) signal after a stage of IF signal amplification to produce a baseband signal.

55. The sensor of claim 1 wherein the microcontroller is configured to control digital amplification of one or more baseband signals derived from the received reflected ones of the emitted radio frequency pulses.

56. The sensor of claim 1 wherein the microcontroller is configured to control digital filtering of one or more signals or baseband signals derived from the received reflected ones of the emitted radio frequency pulses.

\* \* \* \* \*